United States Patent
Vaishnav et al.

(10) Patent No.: US 12,189,021 B2
(45) Date of Patent: Jan. 7, 2025

(54) RADAR-BASED TARGET TRACKER

(71) Applicant: Infineon Technologies AG, Neubiberg (DE)

(72) Inventors: Prachi Vaishnav, Unterhaching (DE); Avik Santra, Munich (DE); Lorenz Ferdinand Wilhelm Weiland, Munich (DE)

(73) Assignee: Infineon Technologies AG, Neubiberg (DE)

( * ) Notice: Subject to any disclaimer, the term of this patent is extended or adjusted under 35 U.S.C. 154(b) by 401 days.

(21) Appl. No.: 17/590,587

(22) Filed: Feb. 1, 2022

(65) Prior Publication Data
US 2022/0260702 A1    Aug. 18, 2022

Related U.S. Application Data

(60) Provisional application No. 63/150,670, filed on Feb. 18, 2021.

(51) Int. Cl.
    *G01S 13/72*      (2006.01)
    *G01S 7/41*      (2006.01)
    *G01S 13/58*      (2006.01)

(52) U.S. Cl.
    CPC ............ *G01S 13/726* (2013.01); *G01S 7/415* (2013.01); *G01S 13/584* (2013.01)

(58) Field of Classification Search
    CPC ...... G01S 13/726; G01S 7/415; G01S 13/584; G01S 13/34; G01S 13/42
    See application file for complete search history.

(56) References Cited

U.S. PATENT DOCUMENTS 4,241,347 A    12/1980    Albanese et al.
6,147,572 A    11/2000    Kaminski et al.
(Continued)

FOREIGN PATENT DOCUMENTS

CN    1463161 A    12/2003
CN    1716695 A    1/2006
(Continued)

OTHER PUBLICATIONS

"BT24MTR11 Using BGT24MTR11 in Low Power Applications 24 GHz Rader," Application Note AN341, Revision: Rev 1.0, Infineon Technologies AG, Munich, Germany, Dec. 2, 2013, 25 pages.
(Continued)

*Primary Examiner* — Timothy A Brainard
*Assistant Examiner* — Kenneth W Good
(74) *Attorney, Agent, or Firm* — Slater Matsil, LLP

(57) ABSTRACT

In an embodiment, a method for tracking a target includes: receiving raw data from a millimeter-wave radar, the raw data including a plurality of macro-Doppler frames, each macro-Doppler frame having N chirps, where each macro-Doppler frame stretches over a time interval having a first duration; generating micro-Doppler frames from the plurality of macro-Doppler frames, each micro-Doppler frame including L chirps from M macro-Doppler frames, where each micro-Doppler frame stretches over a time interval having a second duration that is longer than the first duration; detecting one or more moving targets based on the macro-Doppler frames; detecting one or more static targets based on the micro-Doppler frames; and tracking a first target as the target transitions from being detected based on the macro-Doppler frames to being detected based on the micro-Doppler frames.

26 Claims, 17 Drawing Sheets

(56) References Cited

U.S. PATENT DOCUMENTS

| | | |
|---|---|---|
| 6,414,631 B1 | 7/2002 | Fujimoto |
| 6,636,174 B2 | 10/2003 | Arikan et al. |
| 7,048,973 B2 | 5/2006 | Sakamoto et al. |
| 7,057,564 B2 | 6/2006 | Tsai et al. |
| 7,171,052 B2 | 1/2007 | Park |
| 7,317,417 B2 | 1/2008 | Arikan et al. |
| 7,596,241 B2 | 9/2009 | Rittscher et al. |
| 7,692,574 B2 | 4/2010 | Nakagawa |
| 7,873,326 B2 | 1/2011 | Sadr |
| 7,889,147 B2 | 2/2011 | Tam et al. |
| 8,228,382 B2 | 7/2012 | Pattikonda |
| 8,497,805 B2 | 7/2013 | Rofougaran et al. |
| 8,659,369 B2 | 2/2014 | Rofougaran et al. |
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,229,102 B1 | 1/2016 | Wright et al. |
| 9,413,079 B2 | 8/2016 | Kamgaing et al. |
| 9,495,600 B2 | 11/2016 | Heu et al. |
| 9,886,095 B2 | 2/2018 | Pothier |
| 9,935,065 B1 | 4/2018 | Baheti et al. |
| 10,775,482 B2 | 9/2020 | Santra et al. |
| 10,795,012 B2 | 10/2020 | Santra et al. |
| 2003/0179127 A1 | 9/2003 | Wienand |
| 2004/0238857 A1 | 12/2004 | Beroz et al. |
| 2006/0001572 A1 | 1/2006 | Gaucher et al. |
| 2006/0049995 A1 | 3/2006 | Imaoka et al. |
| 2006/0067456 A1 | 3/2006 | Ku et al. |
| 2007/0210959 A1 | 9/2007 | Herd et al. |
| 2008/0106460 A1 | 5/2008 | Kurtz et al. |
| 2008/0238759 A1 | 10/2008 | Carocari et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0153428 A1 | 6/2009 | Rofougaran et al. |
| 2009/0315761 A1 | 12/2009 | Walter et al. |
| 2010/0207805 A1 | 8/2010 | Haworth |
| 2011/0299433 A1 | 12/2011 | Darabi et al. |
| 2012/0087230 A1 | 4/2012 | Guo et al. |
| 2012/0092284 A1 | 4/2012 | Rofougaran et al. |
| 2012/0116231 A1 | 5/2012 | Liao et al. |
| 2012/0195161 A1 | 8/2012 | Little et al. |
| 2012/0206339 A1 | 8/2012 | Dahl |
| 2012/0265486 A1 | 10/2012 | Klofer et al. |
| 2012/0268314 A1 | 10/2012 | Kuwahara et al. |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2013/0194128 A1 | 8/2013 | Van Der Merwe |
| 2014/0028542 A1 | 1/2014 | Lovitt et al. |
| 2014/0070994 A1 | 3/2014 | Schmalenberg et al. |
| 2014/0145883 A1 | 5/2014 | Baks et al. |
| 2014/0324888 A1 | 10/2014 | Xie et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0135655 A1 | 5/2016 | Ahn et al. |
| 2016/0146931 A1 | 5/2016 | Rao et al. |
| 2016/0146933 A1 | 5/2016 | Rao et al. |
| 2016/0178730 A1 | 6/2016 | Trotta et al. |
| 2016/0187462 A1 | 6/2016 | Altus et al. |
| 2016/0191232 A1 | 6/2016 | Subburaj et al. |
| 2016/0223651 A1 | 8/2016 | Kamo et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0299215 A1 | 10/2016 | Dandu et al. |
| 2016/0306034 A1 | 10/2016 | Trotta et al. |
| 2016/0320852 A1 | 11/2016 | Poupyrev |
| 2016/0320853 A1 | 11/2016 | Lien et al. |
| 2016/0327633 A1 | 11/2016 | Kumar Y.B. et al. |
| 2016/0334502 A1 | 11/2016 | Ali et al. |
| 2016/0349363 A1 | 12/2016 | Millar et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0060254 A1 | 3/2017 | Molchanov et al. |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0131395 A1 | 5/2017 | Reynolds et al. |
| 2017/0139036 A1 | 5/2017 | Nayyar et al. |
| 2017/0141453 A1 | 5/2017 | Waelde et al. |
| 2017/0170947 A1 | 6/2017 | Yang |
| 2017/0176574 A1 | 6/2017 | Eswaran et al. |
| 2017/0192847 A1 | 7/2017 | Rao et al. |
| 2017/0201019 A1 | 7/2017 | Trotta |
| 2017/0212597 A1 | 7/2017 | Mishra |
| 2017/0364160 A1 | 12/2017 | Malysa et al. |
| 2018/0011180 A1* | 1/2018 | Warnick ............... H01Q 21/064 |
| 2018/0046255 A1 | 2/2018 | Rothera et al. |
| 2018/0071473 A1 | 3/2018 | Trotta et al. |
| 2018/0101239 A1 | 4/2018 | Yin et al. |
| 2019/0011549 A1 | 1/2019 | Mercuri et al. |
| 2019/0094350 A1 | 3/2019 | Baheti et al. |
| 2019/0227156 A1* | 7/2019 | Santra .................... G01S 13/42 |
| 2019/0317190 A1* | 10/2019 | Santra .................... G01S 13/18 |
| 2019/0346548 A1 | 11/2019 | Barkan et al. |
| 2020/0091617 A1 | 3/2020 | Lee et al. |
| 2020/0116850 A1 | 4/2020 | Santra et al. |
| 2022/0214441 A1* | 7/2022 | Labusch ............... G01S 13/536 |
| 2023/0034560 A1* | 2/2023 | Kamann ............... G01S 13/589 |

FOREIGN PATENT DOCUMENTS

| | | |
|---|---|---|
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |
| CN | 203950036 U | 11/2014 |
| DE | 102008054570 A1 | 6/2010 |
| DE | 102011100907 A1 | 1/2012 |
| DE | 102011075725 A1 | 11/2012 |
| DE | 102014118063 A1 | 7/2015 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |

(56) References Cited

FOREIGN PATENT DOCUMENTS

| | | | |
|---|---|---|---|
| JP | 2013521508 | A | 6/2013 |
| JP | 2014055957 | A | 3/2014 |
| KR | 20090063166 | A | 6/2009 |
| KR | 20140082815 | A | 7/2014 |
| KR | 20200070595 | A | 6/2020 |
| WO | 2007060069 | A1 | 5/2007 |
| WO | 2013009473 | A2 | 1/2013 |
| WO | 2016033361 | A1 | 3/2016 |

OTHER PUBLICATIONS

Chen, Xiaolong et al., "Detection and Extraction of Marine Target with Micromotion via Short-Time Fractional Fourier Transform in Sparse Domain," IEEE International Conference on Signal Processing, Communications and Computing, ICSPCC, Aug. 5-8, 2016, 5 pages.

Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.

Chioukh, Lydia et al., "Noise and Sensitivity of Harmonic Radar Architecture for Remote Sensing and Detection of Vital Signs", IEEE Transactions on Microwave Theory and Techniques, vol. 62, No. 9, Sep. 2014, pp. 1847-1855.

Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.

Deacon, Peter et al., "Frequency Modulated Continuous Wave (FMCW) Radar," Design Team 6 Technical Lecture, Nov. 9, 2011, 27 pages.

Dham, Vivek "Programming Chirp Parameters in TI Radar Devices," Application Report SWRA553, Texas Instruments, May 2017, 15 pages.

Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.

Gigie, Andrew et al., "Novel Approach for Vibration Detection Using Indented Radar, Progess in Electromagnetic Research C", vol. 87, pp. 147-162, Oct. 4, 2018.

Gouveia, Carolina et al., "A Review on Methods for Random Motion Detection and Compensation in Bio-Radar Systems", Sensors, MDPI, Jan. 31, 2019, 17 pages.

Gu, Changzhan et al., "Assessment of Human Respiration Patterns via Noncontact Sensing Using Doppler Multi-Radar System", Sensors Mar. 2015, 15(3), 6383-6398, doi: 10.3390/s150306383, 17 pages.

Gu, Changzhan et al., "Deep Neural Network based Body Movement Cancellation for Doppler Radar Vital Sign Detection", IEEE MTT-S International Wireless Symposium (IWS) May 19-22, 2019, 3 pages.

Gu, Changzhu "Short-Range Noncontact Sensors for Healthcare and Other Emerginng Applications: A Review", Sensors, MDPI, Jul. 26, 2016, 24 pages.

Gu, Changzhan et al., "From Tumor Targeting to Speed Monitoring", IEEE Microwave Magazine, ResearchGate, Jun. 2014, 11 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Hu, Wei et al., "Noncontact Accurate Measurement of Cardiopulmonary Activity Using a Compact Quadrature Doppler Radar Sensor", IEEE Transactions on Biomedical Engineering, vol. 61, No. 3, Mar. 2014, pp. 725-735.

Immoreev, I. Ya. "Ultrawideband Radars: Features and Capabilities", Journal of Communications Technology and Electronics, ISSN: 1064-2269, vol. 54, No. 1, Feb. 8, 2009, pp. 1-26.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Killedar, Abdulraheem "XWR1xxx Power Management Optimizations—Low Cost LC Filter Solution," Application Report SWRA577, Texas Instruments, Oct. 2017, 19 pages.

Kishore, N. et al., "Millimeter Wave Antenna for Intelligent Transportation Systems Application", Journal of Microwaves, Optoelectronics and Electromagnetic Applications, vol. 17, No. 1, Mar. 2018, pp. 171-178.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Li, Changzhi et al., "A Review on Recent Advances in Doppler Radar Sensors for Noncontact Healthcare Monitoring", IEEE Transactions on Microwave Theory and Techniques, vol. 61, No. 5, May 2013, pp. 2046-2060.

Li, Changzhi et al., "A Review on Recent Progress of Portable Short-Range Noncontact Microwave Radar Systems", IEEE Transactions on Microwave Theory and Techniques, vol. 65, No. 5, May 2017, pp. 1692-1706.

Li, Changzhi et al., "Random Body Movement Cancellation in Doppler Radar Vital Sign Detection", IEEE Transactions on Microwave Theory and Techniques, vol. 56, No. 12, Dec. 2008, pp. 3143-3152.

Li, Changzhi et al., "Robust Overnight Monitoring of Human Vital Signs by a Non-contact Respiration and Heartbeat Detector", IEEE Proceedings of the 28th EMBS Annual International Conference, FrA05.5, Aug. 30-Sep. 3, 2006, 4 pages.

Li, Changzhi "Vital-sign monitoring on the go", Sensors news and views, www.nature.com/naturelectronics, Nature Electronics, vol. 2, Jun. 2019, 2 pages.

Lim, Soo-Chul et al., "Expansion of Smartwatch Touch Interface from Touchscreen to Around Device Interface Using Infrared Line Image Sensors," Sensors 2015, ISSN 1424-8220, vol. 15, 16642-16653, doi:10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Massagram, Wansuree et al., "Assessment of Heart Rate Variability and Respiratory Sinus Arrhythmia via Doppler Radar", IEEE Transactions on Microwave Theory and Techniques, vol. 57, No. 10, Oct. 2009, pp. 2542-2549.

Mercuri, Marco et al., "Vital-sign monitoring and spatial tracking of multiple people using a contactless radar-based sensor", Nature Electronics, vol. 2, Articles, https://doi.org/10.1038/s41928-019-0258-6, Jun. 2019, 13 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Mostov, K., et al., "Medical applications of shortwave FM radar: Remote monitoring of cardiac and respiratory motion", Am. Assoc. Phys. Med., 37(3), Mar. 2010, pp. 1332-1338.

Oguntala, G et al., "Indoor location identification technologies for real-time IoT-based applications: an inclusive survey", Elsevier Inc., http://hdl.handle.net/10454/16634, Oct. 2018, 21 pages.

Peng, Zhengyu et al., "A Portable FMCW Interferometry Radar with Programmable Low-IF Architecture for Localization, ISAR Imaging, and Vial Sign Tracking", IEEE Transactions on Microwave Theory and Techniques, Dec. 15, 2016, 11 pages.

(56) References Cited

OTHER PUBLICATIONS

Qadir, Shahida G., et al., "Focused ISAR Imaging of Rotating Target in Far-Field Compact Range Anechoic Chamber," 14th International Conference on Aerospace Sciences & Aviation Technology, ASAT-14-241-IP, May 24-26, 2011, 7 pages.

Richards, Mark A., "Fundamentals of Radar Signal Processing," McGraw Hill Electronic Engineering, ISBN: 0-07-144474-2, Jun. 2005, 93 pages.

Sakamoto, Takuya et al., "Feature-Based Correlation and Topological Similarity for Interbeat Interval Estimation Using Ultrawideband Radar", IEEE Transactions on Biomedical Engineering, vol. 63, No. 4, Apr. 2016, pp. 747-757.

Santra, Avik et al., "Short-range multi-mode continuous-wave radar for vital sign measurement and imaging", ResearchGate, Conference Paper, Apr. 2018, 6 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Singh, Aditya et al., "Data-Based Quadrature Imbalance Compensation for a CW Doppler Radar System", https://www.researchgate.net/publication/258793573, IEEE Transactions on Microwave Theory and Techniques, Apr. 2013, 7 pages.

Suleymanov, Suleyman, "Design and Implementation of an FMCW Radar Signal Processing Module for Automotive Applications," Master Thesis, University of Twente, Aug. 31, 2016, 64 pages.

Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.

Thayaparan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

Tu, Jianxuan et al., "Fast Acquisition of Heart Rate in Noncontact Vital Sign Radar Measurement Using Time-Window-Variation Technique", IEEE Transactions on Instrumentation and Measurement, vol. 65, No. 1, Jan. 2016, pp. 112-122.

Vinci, Gabor et al., "Microwave Interferometer Radar-Based Vital Sign Detection for Driver Monitoring Systems", IEEE MTT-S International Conference on Microwaves for Intelligent Mobility, Apr. 27-29, 2015, 4 pages.

Vinci, Gabor et al., "Six-Port Radar Sensor for Remote Respiration Rate and Heartbeat Vital-Sign Monitoring", IEEE Transactions on Microwave Theory and Techniques, vol. 61, No. 5, May 2013, pp. 2093-2100.

Wang, Fu-Kang et al., "Wrist Pulse Rate Monitor Using Self-Injection-Locked Radar Technology", Biosensors, MDPI, Oct. 26, 2016, 12 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, 1974, pp. 18-34.

Will, Christoph et al., "Advanced Template Matching Algorithm for Instantaneous Heartbeat Detection using Continuous Wave Radar Systems", ResearchGate, May 2017, 5 pages.

Will, Christoph et al., "Human Target Detection, Tracking, and Classification Using 24-GHz FMCW Radar", IEEE Sensors Journal, vol. 19, No. 17, Sep. 1, 2019, pp. 7283-7299.

Will, Christoph et al., "Local Pulse Wave Detection using Continuous Wave Radar Systems", IEEE Journal of Electromagnetics, RF and Microwaves in Medicine and Biology, Oct. 25, 2017, 9 pages.

Will, Christoph et al., "Radar-Based Heart Sound Detection", Scientific Reports, www.nature.com/scientificreports, Jul. 26, 2018, 15 pages.

Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, Apr. 15, 2014, 11 pages.

\* cited by examiner

RADAR-BASED TARGET TRACKER

CROSS-REFERENCE TO RELATED APPLICATIONS

This application claims the benefit of U.S. Provisional Application No. 63/150,670, entitled "Radar-Based Target Tracker," and filed on Feb. 18, 2021, which application is hereby incorporated herein by reference.

TECHNICAL FIELD

The present disclosure relates generally to an electronic system and method, and, in particular embodiments, to a radar-based target tracker.

BACKGROUND

Applications in the millimeter-wave frequency regime have gained significant interest in the past few years due to the rapid advancement in low cost semiconductor technologies, such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at e.g., 24 GHz, 60 GHz, 77 GHz, and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal (also referred to as the echo), and determining a distance based on a time delay and/or frequency difference between the transmission and reception of the frequency modulated signal. Accordingly, some radar systems include a transmitting antenna for transmitting the radio-frequency (RF) signal, and a receiving antenna for receiving the reflected RF signal, as well as the associated RF circuits used to generate the transmitted signal and to receive the RF signal. In some radar systems, multiple antennas may be used to implement directional beams using phased array techniques. A multiple-input and multiple-output (MIMO) configuration with multiple chipsets can be used to perform coherent and non-coherent signal processing.

SUMMARY

In accordance with an embodiment, a method for tracking a target includes: receiving raw data from a millimeter-wave radar, the raw data including a plurality of macro-Doppler frames, each macro-Doppler frame having N chirps, N being a positive integer greater than 1, where each macro-Doppler frame stretches over a time interval having a first duration; generating micro-Doppler frames from the plurality of macro-Doppler frames, each micro-Doppler frame including L chirps from M macro-Doppler frames, M being a positive integer greater than 1, L being a positive integer greater than 1, where each micro-Doppler frame stretches over a time interval having a second duration that is longer than the first duration; detecting one or more moving targets based on the macro-Doppler frames; detecting one or more static targets based on the micro-Doppler frames; and tracking a first target as the target transitions from being detected based on the macro-Doppler frames to being detected based on the micro-Doppler frames.

In accordance with an embodiment, a method includes: receiving raw data from a millimeter-wave radar, the raw data including a plurality of macro-Doppler frames, each macro-Doppler frame having N chirps, N being a positive integer greater than 1, where each macro-Doppler frame stretches over a time interval having a first duration; generating micro-Doppler frames from the plurality of macro-Doppler frames, each micro-Doppler frame including L chirps from M macro-Doppler frames, M being a positive integer greater than 1, L being a positive integer greater than 1, where each micro-Doppler frame stretches over a time interval having a second duration that is longer than the first duration; detecting one or more moving targets based on the macro-Doppler frames; and detecting one or more static targets based on the micro-Doppler frames, where the second duration is selected to allow the micro-Doppler frames to include vital sign content of the one or more static targets.

In accordance with an embodiment, a millimeter-wave radar includes: a transmitting antenna; a plurality of receiving antennas; a radar sensor configured to: transmit radar signals using the transmitting antenna, and receive reflected radar signals using the plurality of receiving antennas; and a processor configured to: receive raw data from the radar sensor, the raw data including a plurality of macro-Doppler frames, each macro-Doppler frame having N chirps, N being a positive integer greater than 1, where each macro-Doppler frame stretches over a time interval having a first duration, generate micro-Doppler frames from the plurality of macro-Doppler frames, each micro-Doppler frame including L chirps from M macro-Doppler frames, M being a positive integer greater than 1, L being a positive integer greater than 1, where each micro-Doppler frame stretches over a time interval having a second duration that is longer than the first duration; detect one or more moving targets based on the macro-Doppler frames; detect one or more static targets based on the micro-Doppler frames; and track a first target as the first target transitions from being detected based on the macro-Doppler frames to being detected based on the micro-Doppler frames.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

The making and using of the embodiments disclosed are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

Embodiments of the present invention will be described in a specific context, a millimeter-wave radar-based tracker for people sensing, e.g., in an indoor environment. Embodiments of the present invention may be used for tracking other targets (e.g., animals, vehicles, robots, etc.) and/or may operate in regimes different than millimeter-wave. Some embodiments may be used outdoors.

In an embodiment of the present invention, a millimeter-wave radar is used to detect and track human targets that transition between a moving state and an static (idle) state in an indoor environment. A macro-Doppler processing chain is used to track human targets moving using macro-Doppler frames at a macro-Doppler frame rate. A micro-Doppler processing chain is used to track human targets that are static (e.g., seating, standing idle, or lying) using micro-Doppler frames at a micro-Doppler frame rate that is slower than the macro-Doppler frame rate. In some embodiments, the micro-Doppler frame rate is filtered to allow energy at a frequency range associated with human vital signs (e.g., between 0.5 Hz and 5 Hz).

Figure 1:
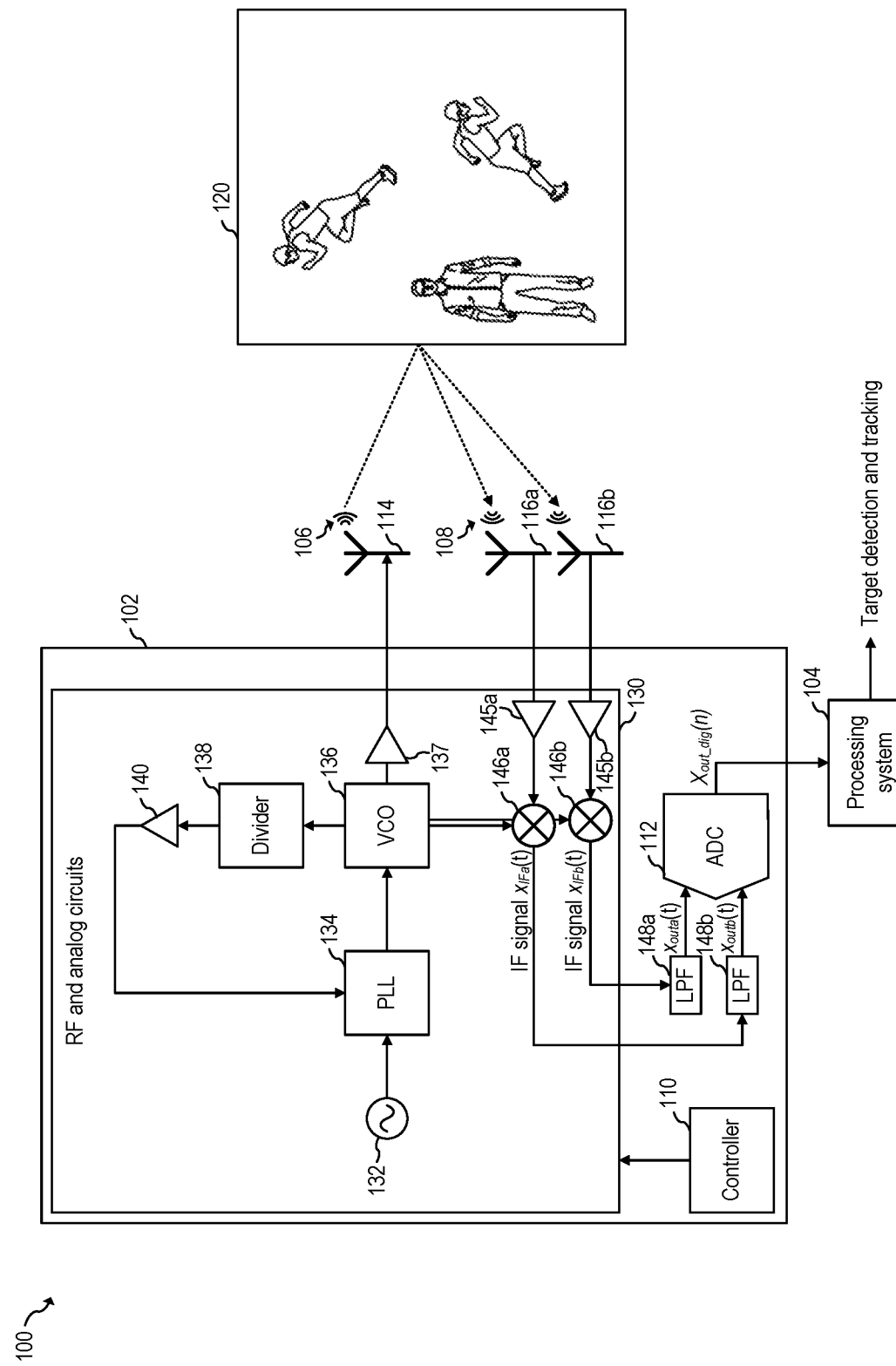
FIG. 1 shows a schematic diagram of a millimeter-wave radar system, according to an embodiment of the present invention.

A radar, such as a millimeter-wave radar, may be used to detect and track humans. For example, FIG. 1 shows a schematic diagram of millimeter-wave radar system 100, according to an embodiment of the present invention. Millimeter-wave radar system 100 includes millimeter-wave radar sensor 102 and processing system 104.

During normal operation, millimeter-wave radar sensor 102 operates as a frequency-modulated continuous-wave (FMCW) radar sensor and transmits a plurality of TX radar signals 106, such as chirps, towards scene 120 using one or more transmitter (TX) antenna 114. The radar signals 106 are generated using RF and analog circuits 130. The radar signals 106 may be, e.g., in the 20 GHz to 122 GHz range. Other frequencies may also be used.

The objects in scene 120 may include one or more static or moving objects, such as cars, motorcycles, bicycles, trucks, and other vehicles, idle and moving humans and animals, furniture, machinery, mechanical structures, walls and other types of structures. Other objects may also be present in scene 120.

The radar signals 106 are reflected by objects in scene 120. The reflected radar signals 108, which are also referred to as the echo signal, are received by a plurality of receiving (RX) antennas. RF and analog circuits 130 processes the received reflected radar signals 108 using, e.g., band-pass filters (BPFs), low-pass filters (LPFs), mixers, low-noise amplifier (LNA), and/or intermediate frequency (IF) amplifiers in ways known in the art to generate an analog signal $x_{outa}(t)$ and $x_{outb}(t)$.

The analog signal $x_{outa}(t)$ and $x_{outb}(t)$ are converted to raw digital data $x_{out\_dig}(n)$ using analog-to-digital converter (ADC) 112. The raw digital data $x_{out\_dig}(n)$ is processed by processing system 104 to detect targets and their position. In some embodiments, processing system 104 may also be used to identify, classify, and/or track one or more targets in scene 120.

Although FIG. 1 illustrates a radar system with two receiver antennas 116 (antennas 116a and 116b), it is understood that more than two receiver antennas 116, such as three or more, may also be used.

Although FIG. 1 illustrates a radar system with a single transmitter antenna 114, it is understood that more than one transmitter antenna 114, such as two or more, may also be used.

Controller no controls one or more circuits of millimeter-wave radar sensor 102, such as RF and analog circuit 130 and/or ADC 112. Controller 110 may be implemented, e.g., as a custom digital or mixed signal circuit, for example. Controller 110 may also be implemented in other ways, such as using a general purpose processor or controller, for example. In some embodiments, processing system 104 implements a portion or all of controller no.

Processing system 104 may be implemented with a general purpose processor, controller or digital signal processor (DSP) that includes, for example, combinatorial circuits coupled to a memory. In some embodiments, processing system 104 may be implemented as an application specific integrated circuit (ASIC). In some embodiments, processing system 104 may be implemented with an ARM, RISC, or x86 architecture, for example. In some embodiments, processing system 104 may include an artificial intelligence (AI) accelerator. Some embodiments may use a combination of hardware accelerator and software running on a DSP or general purpose microcontroller. Other implementations are also possible.

In some embodiments, millimeter-wave radar sensor 102 and a portion or all of processing system 104 may be implemented inside the same integrated circuit (IC). For example, in some embodiments, millimeter-wave radar sensor 102 and a portion or all of processing system 104 may be implemented in respective semiconductor substrates that are integrated in the same package. In other embodiments, millimeter-wave radar sensor 102 and a portion or all of processing system 104 may be implemented in the same monolithic semiconductor substrate. In some embodiments, millimeter-wave radar sensor 102 and processing system 104 are implemented in respective integrated circuits. In some embodiments, a plurality of integrated circuits is used to implement millimeter-wave radar sensor 102. In some embodiments, a plurality of integrated circuits is used to implement processing system 104. Other implementations are also possible.

As a non-limiting example, RF and analog circuits 130 may be implemented, e.g., as shown in FIG. 1. During normal operation, voltage-controlled oscillator (VCO) 136 generates radar signals, such as a linear frequency chirps (e.g., from 57 GHz to 64 GHz, or from 76 GHz to 77 GHz), which are transmitted by transmitting antenna 114. The VCO 136 is controlled by PLL 134, which receives a reference clock signal (e.g., 80 MHz) from reference oscillator 132. PLL 134 is controlled by a loop that includes frequency divider 138 and amplifier 140. Amplifier 137 may be used to drive transmitting antenna 114.

The TX radar signals 106 transmitted by transmitting antenna 114 are reflected by objects in scene 120 and received by receiving antennas 116a and 116b. The echo received by receiving antennas 116a and 116b are mixed with a replica of the signal transmitted by transmitting antenna 114 using mixer 146a and 146b, respectively, to produce respective intermediate frequency (IF) signals $x_{IFa}$(t) $x_{IFb}$(t) (also known as beat signals). In some embodiments, the beat signals $x_{IFa}$(t) and $x_{IFb}$(t) have a bandwidth between 10 kHz and 1 MHz. Beat signals with a bandwidth lower than 10 kHz or higher than 1 MHz is also possible. Amplifiers 145a and 145b may be used to receive the reflected radar signals from antennas 116a and 116b, respectively.

Beat signals $x_{IFa}$(t) $x_{IFb}$(t) are filtered with respective low-pass filters (LPFs) 148a and 148b and then sampled by ADC 112. ADC 112 is advantageously capable of sampling the filtered beat signals $x_{outa}$(t) $x_{outb}$(t) with a sampling frequency that is much smaller than the frequency of the signal received by receiving antennas 116a and 116b. Using FMCW radars, therefore, advantageously allows for a compact and low cost implementation of ADC 112, in some embodiments.

The raw digital data $x_{out\_dig}$(n), which in some embodiments include the digitized version of the filtered beat signals $x_{outa}$(t) and $x_{outb}$(t), is (e.g., temporarily) stored, e.g., in matrices of $N_c \times N_s$ per receiving antenna 116, where $N_c$ is the number of chirps considered in a frame and $N_s$ is the number of transmit samples per chirp, for further processing by processing system 104.

In some embodiments, ADC 112 is a 12-bit ADC with multiple inputs. ADCs with higher resolution, such as 14-bits or higher, or with lower resolution, such as 10-bits, or lower, may also be used. In some embodiments, an ADC per receiver antenna may be used. Other implementations are also possible.

Figure 2:
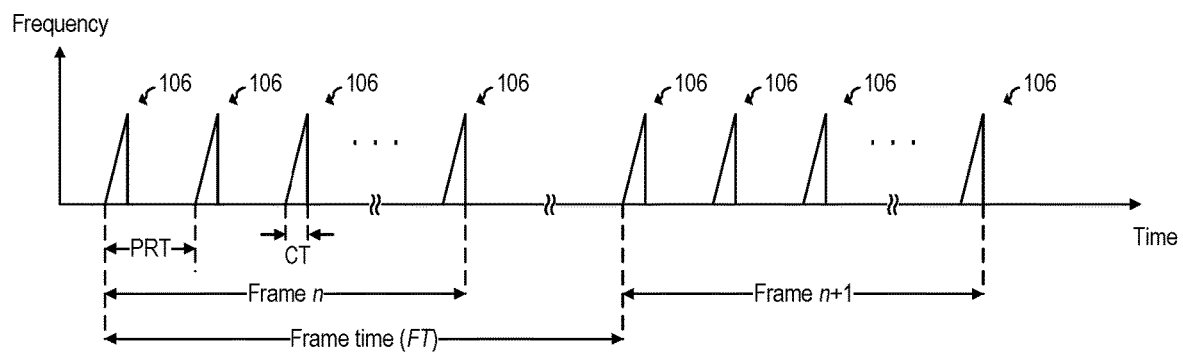
FIG. 2 shows a sequence of chirps transmitted by the TX antenna of FIG. 1, according to an embodiment of the present invention.

FIG. 2 shows a sequence of chirps 106 transmitted by TX antenna 114, according to an embodiment of the present invention. As shown by FIG. 2, chirps 106 are organized in a plurality of frames (also referred to as physical frames) and may be implemented as up-chirps. Some embodiments may use down-chirps or a combination of up-chirps and down-chirps, such as up-down chirps and down-up chirps. Other waveform shapes may also be used.

As shown in FIG. 2, each frame may include a plurality of chirps 106 (also referred to, generally, as pulses). For example, in some embodiments, the number of pulses in a frame is 16. Some embodiments may include more than 16 pulses per frame, such as 20 pulses, 32 pulses, or more, or less than 16 pulses per frame, such as 10 pulses, 8 pulses, 4 or less. In some embodiments, each frame includes only a single pulse.

In some embodiments, frames are repeated every FT time. In some embodiments, FT time is 50 ms. A different FT time may also be used, such as more than 50 ms, such as 60 ms, 100 ms, 200 ms, or more, or less than 50 ms, such as 45 ms, 40 ms, or less.

In some embodiments, the FT time is selected such that the time between the beginning of the last chirp of frame n and the beginning of the first chirp of frame n+1 is equal to PRT. Other embodiments may use or result in a different timing.

The time between chirps of a frame is generally referred to as pulse repetition time (PRT). In some embodiments, the PRT is 5 ms. A different PRT may also be used, such as less than 5 ms, such as 4 ms, 2 ms, or less, or more than 5 ms, such as 6 ms, or more.

The duration of the chirp (from start to finish) is generally referred to as chirp time (CT). In some embodiments, the chirp time may be, e.g., 64 μs. Higher chirp times, such as 128 μs, or higher, may also be used. Lower chirp times, may also be used.

In some embodiments, the chirp bandwidth may be, e.g., 4 GHz. Higher bandwidth, such as 6 GHz or higher, or lower bandwidth, such as 2 GHz, 1 GHz, or lower, may also be possible.

In some embodiments, the sampling frequency of millimeter-wave radar sensor 102 may be, e.g., 1 MHz. Higher sampling frequencies, such as 2 MHz or higher, or lower sampling frequencies, such as 500 kHz or lower, may also be possible.

In some embodiments, the number of samples used to generate a chirp may be, e.g., 64 samples. A higher number of samples, such as 128 samples, or higher, or a lower number of samples, such as 32 samples or lower, may also be used.

Detecting and tracking human targets in an indoor environment may be desirable for a variety of reasons, such as security reasons (e.g., detecting an intruder), marketing reasons (e.g., studying shopper behavior), productivity reasons (e.g., studying employees in an assembly line), automation reasons (e.g., taking an action based on the presence or trajectory of a target, such as a human), and/or research and development reasons, for example.

Conventional methods for tracking a target assume that that the target is a single point in the range-Doppler map. In a conventional range-Doppler processing chain, the cluster of detections obtained is used to obtain a single bin in a range-Doppler image to determine range and Doppler components of the target detected. Such single bin is then fed into the tracker for tracking the target. For example, in conventional radar signal processing, the range, Doppler and angle of arrival may be detected for the single point target. Such components are then fed into the tracker for tracking purposes.

The motion model for a conventional tracker may be expressed as $$\begin{cases} px(k+1) = px(k) + \Delta t \cdot vx(k) \\ py(k+1) = py(k) + \Delta t \cdot vy(k) \\ vx(k+1) = vx(k) \\ vy(k+1) = vy(k) \end{cases} \quad (1)$$

where k represents a discrete time step, $\Delta t$ is the time between each time step, px is the position of the (e.g., centroid of) target in the x direction, py is the position of the (e.g., centroid of) target in the y direction, vx is the velocity of the target in the x direction, and vy is the velocity of the target in the y direction.

Figure 3:
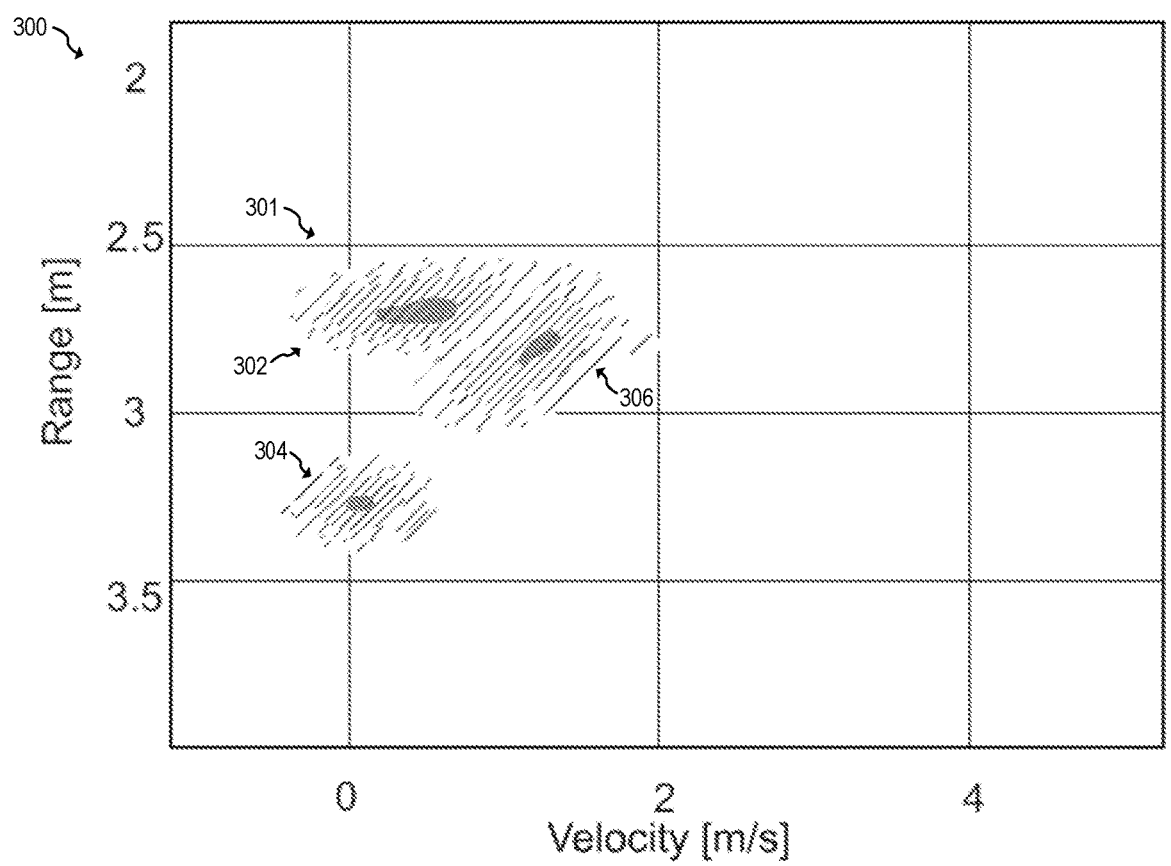
FIG. 3 shows an exemplary range-Doppler map of a moving human captured with a millimeter-wave radar system.

In some radar systems, such as in some millimeter-wave radar systems, a human target may exhibit a double spread across range and Doppler bins as reflections are received from different parts of the human body during movement of the human target. For example, FIG. 3 shows exemplary range-Doppler map 300 of moving human 301 captured with a millimeter-wave radar system. As shown in FIG. 3, a human target may exhibit peaks at different locations of the range-Doppler map corresponding to different portions of the human target body, such as the right foot 304, left foot 302, and torso and hands 306.

Figure 4:
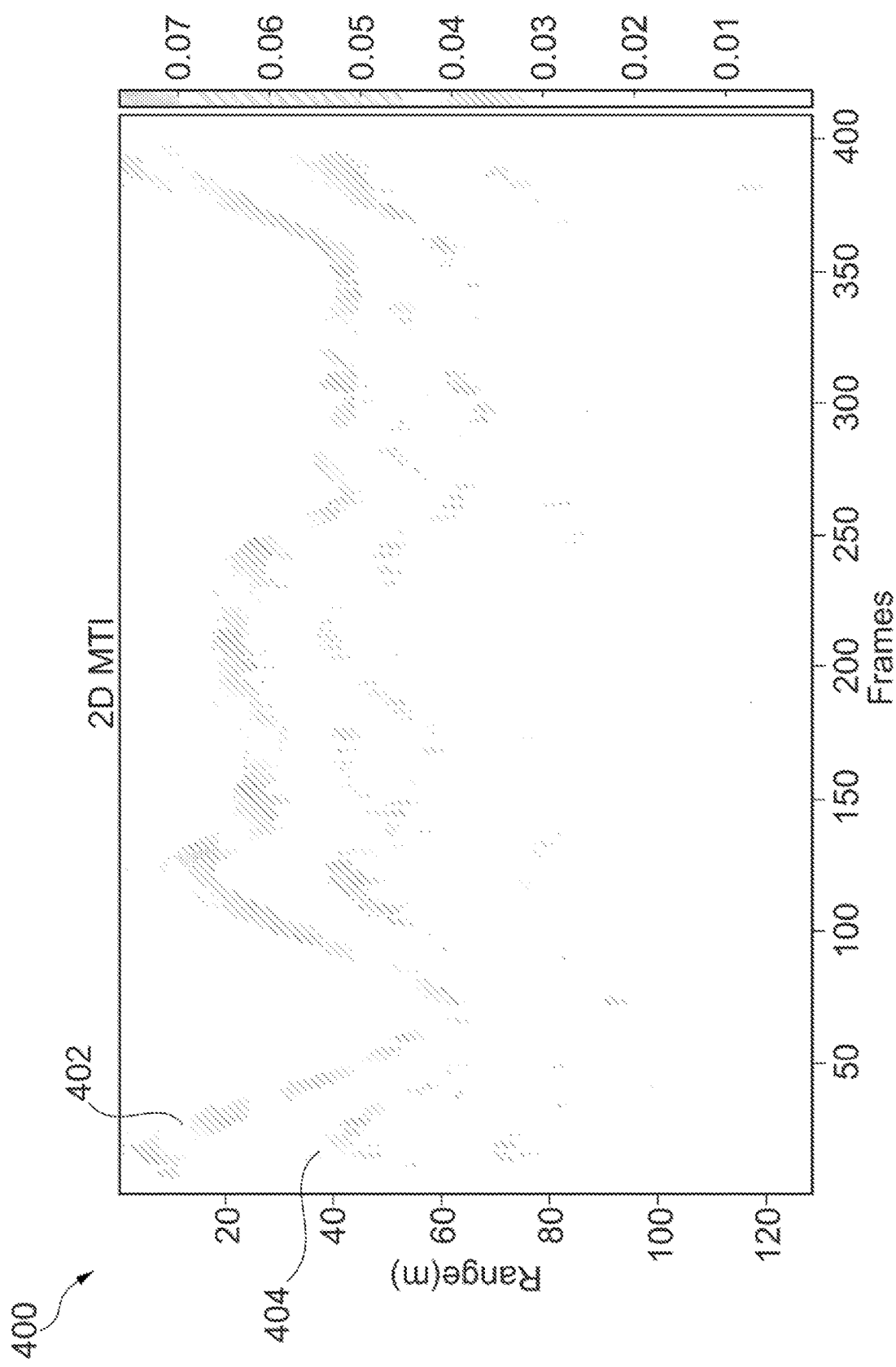
FIG. 4 shows an exemplary range spectrogram of a human target moving in a zigzag manner in an indoor environment surrounded by walls, after two-dimensional (2D) moving target indication (MTI) filtering and coherent integration.

Some radar systems, such as some millimeter-wave radar systems in an indoor environment, may be susceptible to multipath reflections from walls, chairs, and other objects, which may appear as real targets along with the actual human target. For example, FIG. 4 shows exemplary range spectrogram 400 of a human target moving in a zigzag manner in an indoor environment surrounded by walls, after two-dimensional (2D) moving target indication (MTI) filtering and coherent integration. Range spectrogram 400 includes curve 402 corresponding to a human target, and curve 404 corresponding to a multipath reflection. Range spectrogram 400 also includes additional multipath reflection curves.

As shown by curve 404, continuous multipath reflections obtained from a wall remain observable (although with lower energy than curve 402) after applying a conventional MTI filter to remove static objects. The similarity in Doppler signatures of multipath reflection (e.g., 404) with respect to curve 402 may cause detection of ghost target during radar signal processing.

Figure 5:
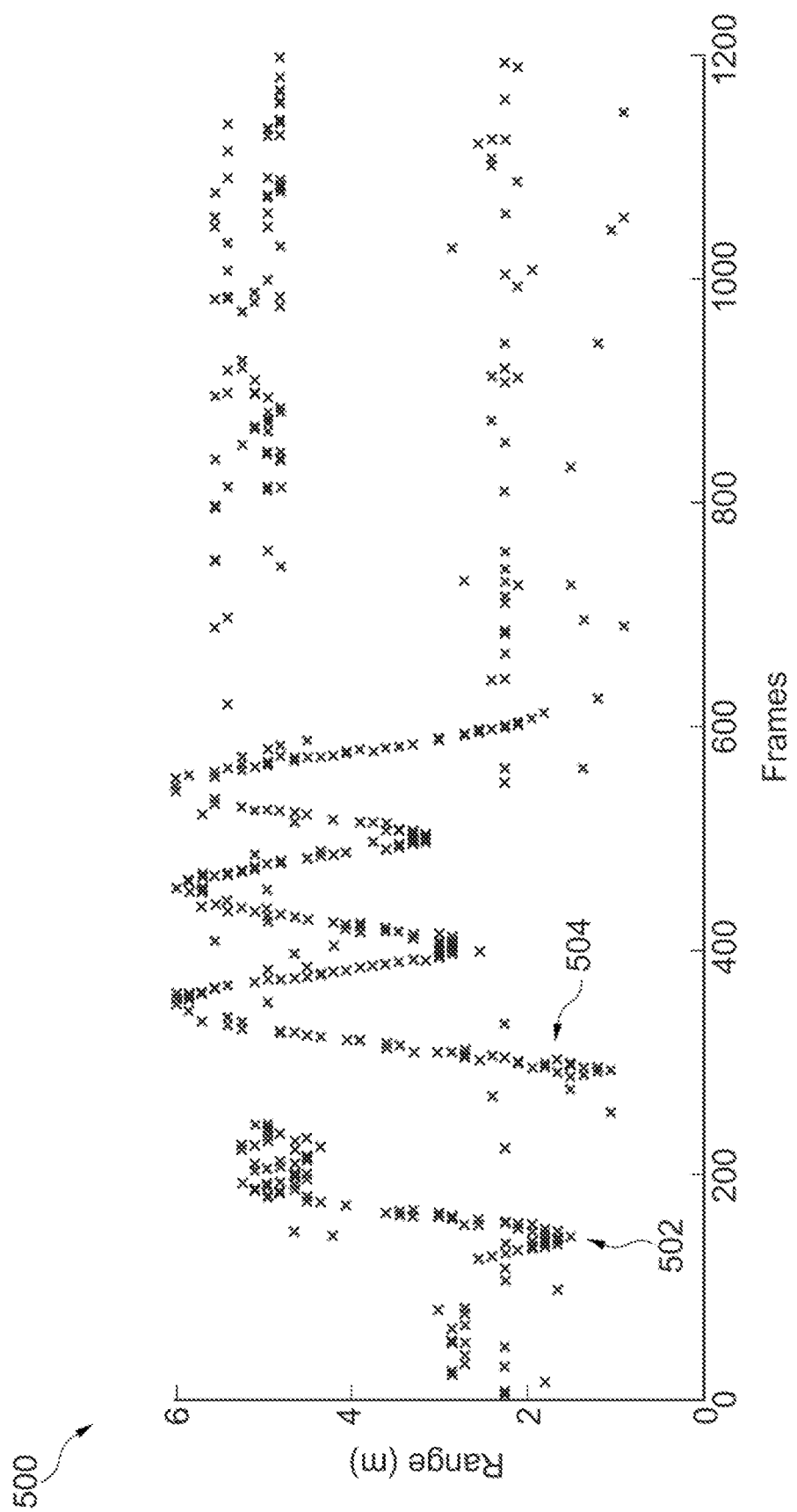
FIG. 5 shows an exemplary range plot after pre-processing of raw digital data form a millimeter-wave radar.

Even though conventional moving target annihilators, such as MTI filters may not fully remove multipath reflections, such annihilators may be effective at removing static objects such as walls. For example, FIG. 5 shows exemplary range plot 500 after pre-processing of raw digital data (including Range Doppler, MTI, Beam forming, CFAR, and DBSCAN) from millimeter-wave radar. Range plot 500 includes detections of human 502 and human 504 in an indoor environment having a wall at about 6 meters from the millimeter-wave radar sensor. Frames of 0.1 ms are used in range plot 500.

At about frame 150, human 502 walks towards the millimeter-wave radar sensor (from about 2.5 meters to about 1.5 meters), and then turns and walks away from the millimeter-wave radar sensor and towards the wall. At about frame 200, human 502 becomes idle, and remains idle for the remaining frames.

Between frames about 300 to about 600, human 504 walks in a zigzag manner towards the millimeter-wave radar sensor and away from the millimeter-wave radar sensor.

As shown in FIG. 5, MTI filtering successfully removes the presence of the wall from the range plot (where the wall is located at 6 meters from the millimeter-wave radar sensor). As also shown in FIG. 5, human 504 is detected as human 504 moves towards and away from the millimeter-wave radar sensor (between frames about 300 to about 600). Human 502 is also detected while moving towards and away from the millimeter-wave radar sensor (between frames about 150 to about 200) but is not detected after human 502 becomes idle (after frame about 200). The missed detection of human 502 may be cause by low SNR associated with human 502 once human 502 becomes idle.

In an embodiment of the present invention, a first processing chain is used for detecting moving targets, and a second processing chain is used for detecting static targets. The detected targets from the first and second processing chains are then merged and tracked using a tracker, such as an interactive multiple model (IMM) tracker. By using a processing chain dedicated for detecting static targets, some embodiments advantageously increase the SNR of static targets and remove influence of moving targets into static detections, thereby advantageously improving detection of static targets. In some embodiments, idle humans are distinguished from static objects (such as a wall) by focusing the signal processing analysis of the second processing chain in a frequency range associated with vital signals of human targets, such as heart-beat rate and respiration rate. In some embodiments, the first processing chain is also capable of detecting high SNR static targets.

In some embodiments, static humans (e.g., seating humans, standing humans, and/or lying humans) are distinguished from static objects (such as a wall) by tracking targets in a static state only after the target transitions to the static state from a moving state.

By using two processing chains for detecting moving and static targets, some embodiments advantageously detect static humans (e.g., seating humans, standing humans, and/or lying humans) in mixed scenarios that exhibit moving targets, static humans, and other static objects.

In some embodiments, target detection at the first processing chain and the second processing chain are performed at two different rates. In some embodiments, the tracker operates at a faster rate between the chirp rate of the first processing chains and the chirp rate of the second processing chain. By using a single tracker to track detected targets from the first and second processing chains, some embodiments advantageously achieve seamless detection and tracking of moving as well as static human targets.

Figure 6:
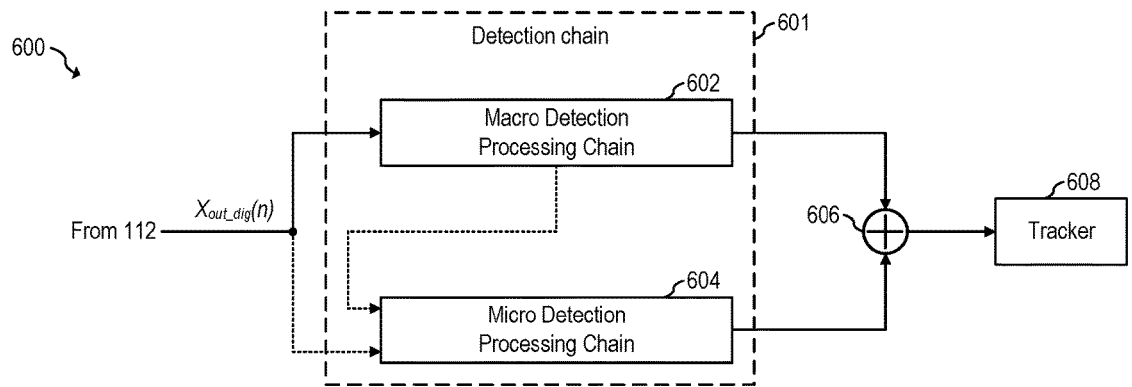
FIG. 6 shows a diagram of an embodiment detection and tracking system for detecting and tracking human targets, according an embodiment of the present invention.

FIG. 6 shows a diagram of embodiment detection and tracking system 600 for detecting and tracking human targets, according an embodiment of the present invention. Detection and tracking system 600 may be implemented by processing system 104.

As shown in FIG. 6, a detection chain 601 is used to detect one or more targets that are tracked by tracker 608. In some embodiments, detection chain 601 includes a macro-Doppler processing chain, and a micro-Doppler and/or vital processing chain, which may be implemented, e.g., as described in U.S. patent application Ser. No. 15/876,769, now U.S. Pat. No. 10,795,012, filed Jan. 22, 2018, entitled "System and Method for Human Behavior Modeling and Power Control using a Millimeter-Wave Radar Sensor," which application is hereby incorporated by reference.

In some embodiments, detection chain includes processing chains 602 and 604. As shown, macro detection processing chain 602 receives raw digital data $x_{out\_dig}(n)$ from ADC 112. In some embodiments, raw digital data $x_{out\_dig}(n)$ includes a datacube of slow-time samples by fast-time samples by number of receiving antennas 116. In some embodiments, the data received by macro detection processing chain 602 is organized in frames having a first frame rate.

Macro-Doppler detection processing chain (also referred to as macro detection processing chain) 602 detects and identifies moving targets and high SNR static targets in the field-of-view of millimeter-wave radar sensor 102. For example, in some embodiments, macro detection processing chain 602 produces an output that includes a set of target parameters associated with the respective detected targets, where each target parameter includes data associated with range, Doppler velocity, and angle of the respective target.

In some embodiments, after MTI filtering in macro detection processing chain 602, only targets with high motion are retained as their energy is varying across Doppler images. Thus, in some embodiments, the set of target parameters do not include target parameters associated with low motion, such as walls, since such targets may be removed, e.g., by MTI filtering, performed by macro detection processing chain 602 (e.g., since, even though a wall may be considered a high SNR object, fluctuations in the motion of a wall, if any, are too low to cause the retention of the wall as a target after MTI filtering).

Micro detection processing chain (also referred to as micro detection processing chain) 604 detects and identifies static targets in the field-of-view of millimeter-wave radar sensor 102. For example, in some embodiments, micro detection processing chain 604 produces an output that includes a set of target parameters associated with the respective detected targets, where each target parameter includes data associated with range and angle of the respective target. In some embodiments, the target parameters generated by micro detection processing chain 604 do not include Doppler velocity, as it may be assumed to be 0 m/s (since the targets detected by micro detection processing chain 604 are static targets).

It is understood that a static target, such as a static human target (e.g., such as a seating human, a standing human, and a lying human), may still exhibit some minor movements, such as associated with respiration and heartbeat rate.

In some embodiments, the targets detected by detection processing chains 602 and 604 are combined and then tracked by a single tracker 608.

In some embodiments, tracker 608 may be implemented as an interactive multiple model (IMM) tracker. Other trackers may also be used.

As shown in FIG. 6, in some embodiments, frames used for macro detection processing chain 602 (also referred to as macro Doppler frames, or macro frames) and frames used for micro detection processing chain 604 (also referred to as micro Doppler frames, or micro frames) may be respectively generated, e.g., directly, from raw digital data $x_{out\_dig}(n)$. In some embodiments, the micro frames may be generated based on the macro frames.

In some embodiments, a sliding window is used for constructing the macro frames and/or the micro frames, which may advantageously decouple physical frame length and physical frame rate for the detection processing chain(s) (e.g., 602 and/or 604). In some embodiments, using a sliding window advantageously increases the collection of energy from static humans, which may increase the SNR of static human targets, thereby advantageously facilitating static human target detection.

In some embodiments, macro detection processing chain 602 and micro detection processing chain 604 operate at different rates. For example, in some embodiments, each of the macro frames used by macro detection processing chain 602 for target detection stretches over a first duration that is shorter than the duration of each of the micro frames used by micro detection processing chain 604. For example, FIG. 7 shows macro frames 702 used for macro detection processing chain 602 and micro frames 704 used for micro detection processing chain 604, according to an embodiment of the present invention.

Figure 7:
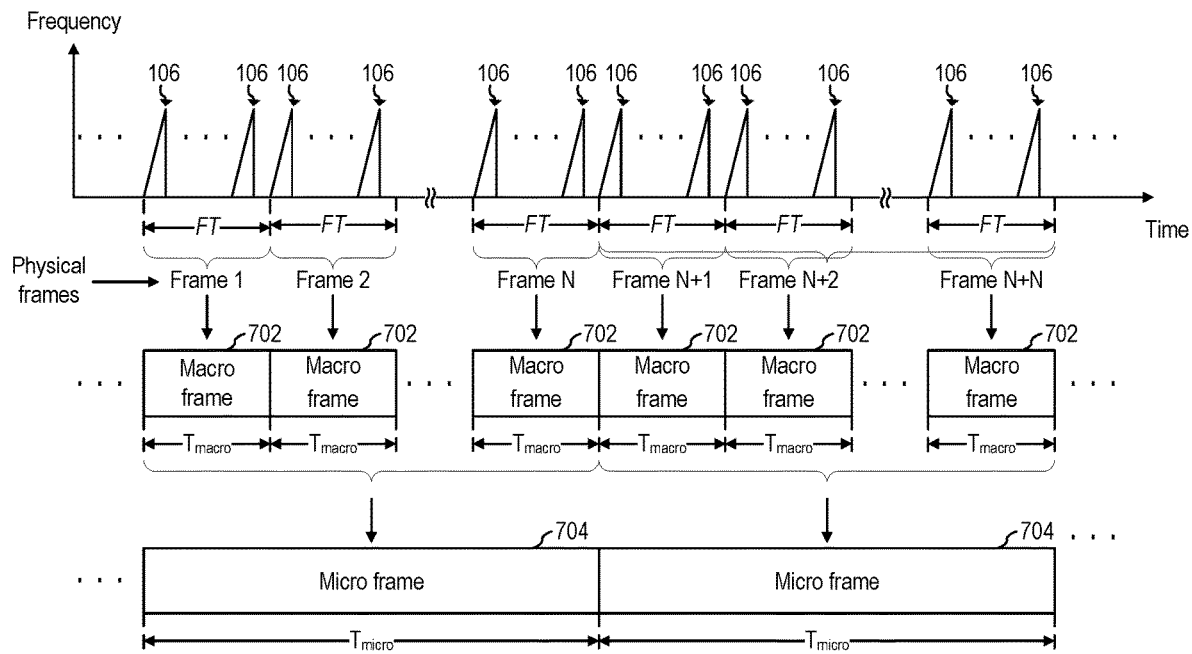
FIG. 7 shows frames used for the macro detection processing chain of FIG. 6 and frames used for the micro detection processing chain of FIG. 6, according to an embodiment of the present invention.

As shown in FIG. 7, each macro frames may correspond to a respective physical frame. For example, in some embodiments, a macro frame 702 may include the same number of chirps as a corresponding physical frame and may have the same duration. For example, in some embodiments, each macro frame 702 includes 32 chirps and stretches over time interval $T_{macro}$, where $T_{macro}$ is equal to FT. For example, in some embodiments, $T_{macro}$ is equal to 0.1 ms, and FT is equal to 0.1 ms.

In some embodiments, each macro frame 702 may include more than 32 chirps, such as 64 chirps, or more, or less than 32 chirps, such as 16 chirps, or less.

In some embodiments, a macro frame may stretch over a time interval that is different (e.g., longer) than FT.

As shown in FIG. 7, micro frames stretch over a time interval $T_{micro}$ that is longer than time interval $T_{macro}$. For example, in some embodiments, each micro frame 704 is generated based on a plurality of macro frames 702 and stretches over a time interval $T_{micro}$ that is a multiple of $T_{macro}$. For example, in some embodiments $T_{micro}$ is equal to P times $T_{macro}$, where P is a positive integer greater than 1, such as 32.

In some embodiments, a micro frame 704 may include the same number of chirps as the macro frames 702. For example, in some embodiments, each macro frame 702 includes 32 chirps and stretches over time interval $T_{macro}$, and each micro frame 702 includes 32 chirps, where the 32 chirps of each micro frame 32 is based on 32 consecutive macro frames 702, respectively. For example, in an embodiment, each macro frame 702 includes 32 chirps and stretches over a time interval $T_{macro}$ equal to 0.1 ms, and each micro frame 704 includes 32 chirps and stretches over a time interval $T_{micro}$ equal to 3.2 s.

In some embodiments, each micro frame 704 may include more than 32 chirps, such as 64 chirps, or more, or less than 32 chirps, such as 16 chirps, or less.

In some embodiments, the number of chirps in a micro frame 704 is different than the number of chirps in a macro frame 702.

Figure 8:
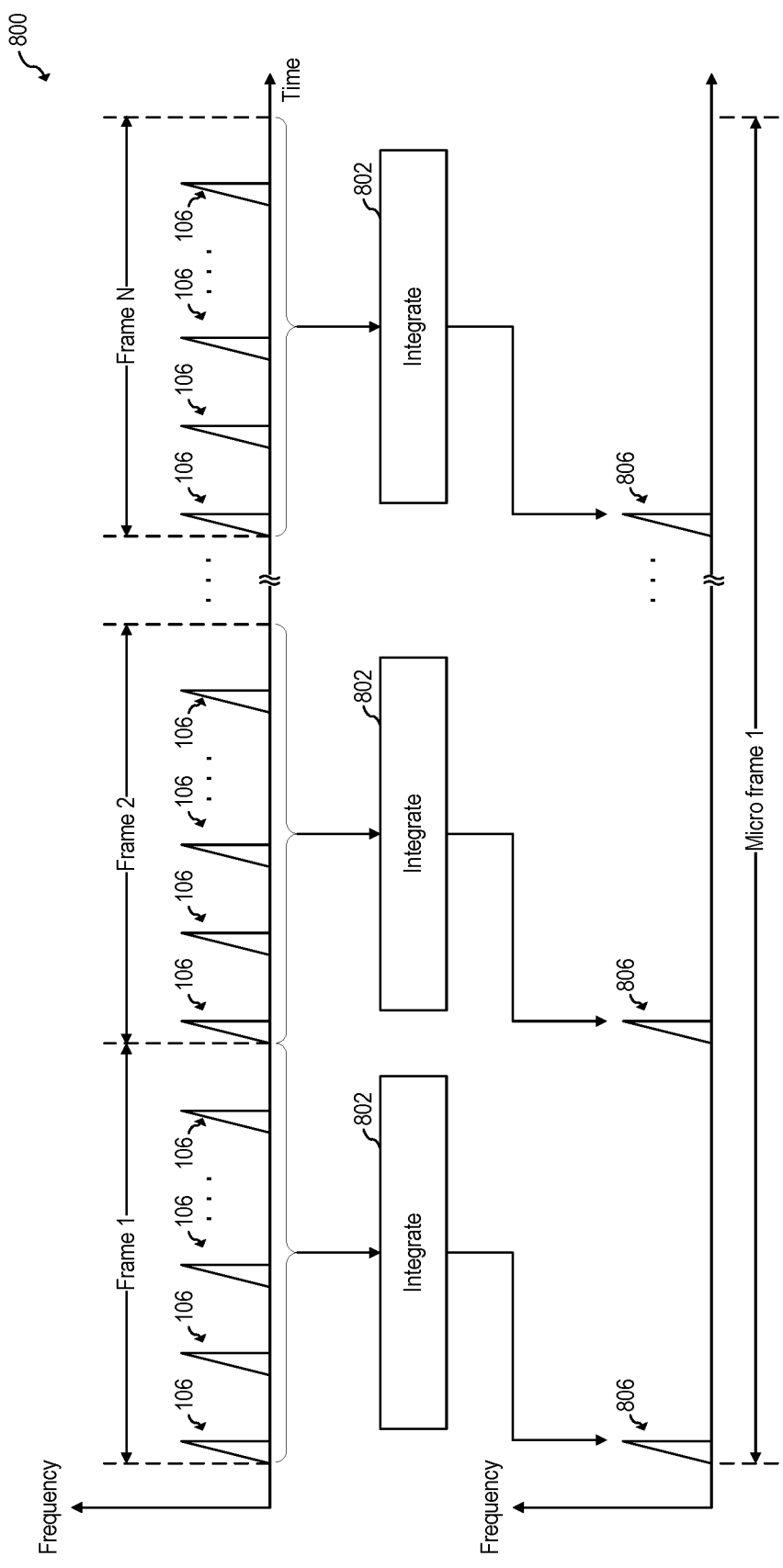
FIGS. 8 and 9 show diagrams embodiment methods for generating micro frames for the micro detection processing chain of FIG. 6, according to an embodiment of the present invention.

FIG. 8 shows a diagram of embodiment method 800 for generating micro frames 704 for micro detection processing chain 604, according to an embodiment of the present invention. Method 800 may be implemented by processing system 104.

During step 802, chirps 106 of a physical frame are integrated to form chirps 806 of a micro frame 704. For example, in some embodiments, all of the chirps of a physical frame are integrated to generate a single chirp 806 of a micro frame. By integrating (e.g., all) chirps of a physical frame to form a chirp of a micro frame, some embodiments advantageously increase the SNR of static targets in the micro frame.

In some embodiments, a subset of chirps 106 is integrated to generate a single chirp 806. For example, in some embodiments, half of the chirps 106 of a physical frame are integrated to generate a chirp 806. In some embodiments, more than half of the chirps 106, or less than half of the chirps 106, are integrated to form generate a chirp 806. In some embodiments, the subset of chirps 106 selected for integration is randomly selected for each consecutive physical frame, which in some embodiments may advantageously improve SNR of static targets.

Although step 802 is described with respect to physical frames, in some embodiments, the chirps of a micro frame 704 may be generated using step 802 from chirps of macro frames.

Figure 9:
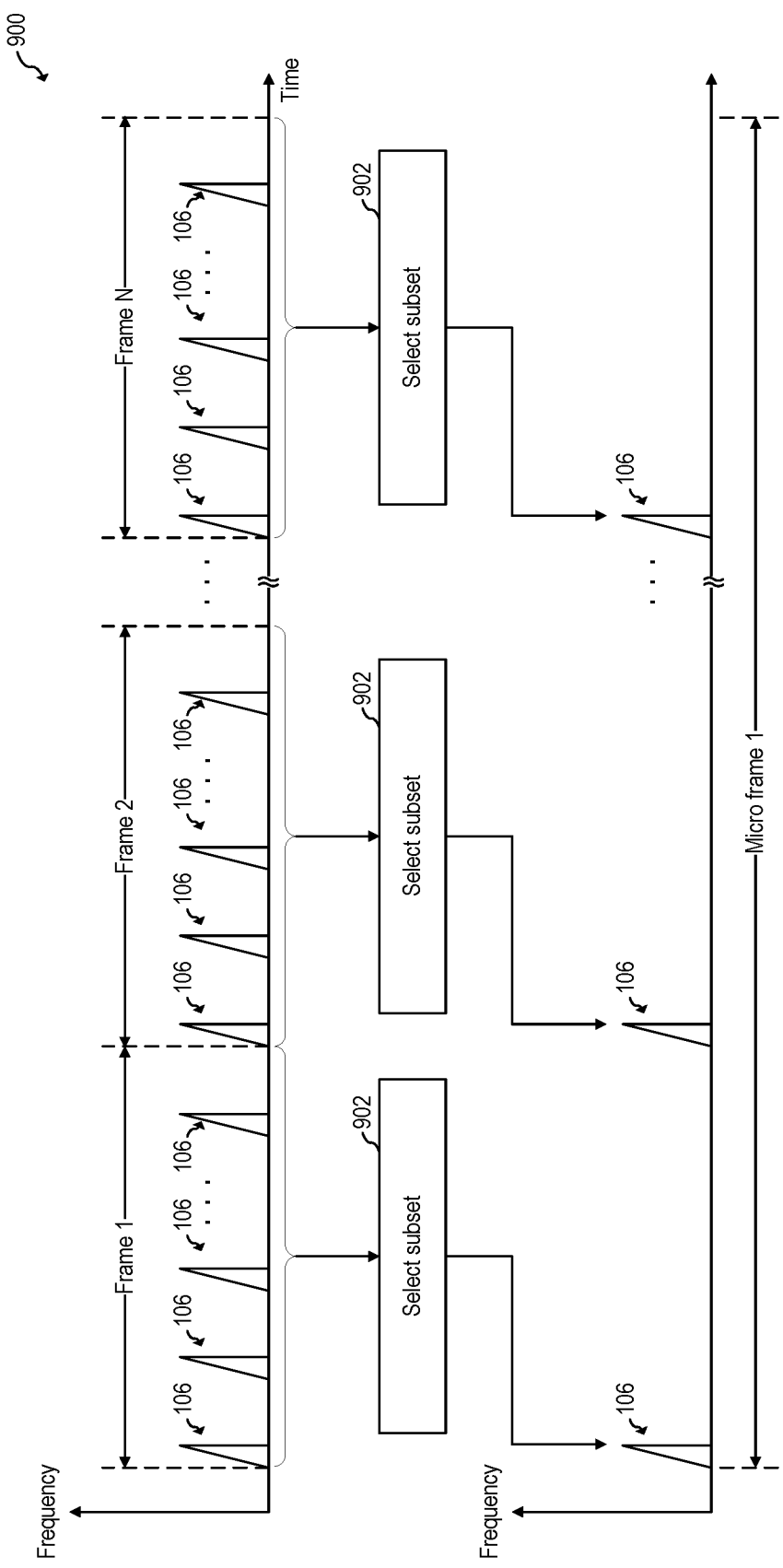

FIG. 9 shows a diagram of embodiment method 900 for generating micro frames 704 for micro detection processing chain 604, according to an embodiment of the present invention. Method 900 may be implemented by processing system 104.

During step 902, one or more chirps 106 of a physical frame are selected to construct a micro frame 704. For example, in some embodiments, the first chirp 106 of each physical frame becomes a chirp of a micro frame 704 (chirps 106 in other locations of the frame may also be used). Thus, in some embodiments, generating a micro frame of 32 chirps includes selecting a chirp from each of 32, e.g., consecutive physical frames. In an embodiment in which 2 chirps are selected from each physical frame, generating a micro frame of 32 chirps includes selecting a chirp from each of 16, e.g., consecutive physical frames.

In some embodiments, which chirp(s) 106 is selected from each physical frame (e.g., the first chirp 106, the last chirp 106, or another chirp between the first chirp 106 and the last chirp 106) is randomly determined, e.g., for each of the consecutive physical frames.

Although step 902 is described with respect to physical frames, in some embodiments, the chirps of a micro frame 704 may be generated using step 902 from chirps of macro frames.

Figure 10:
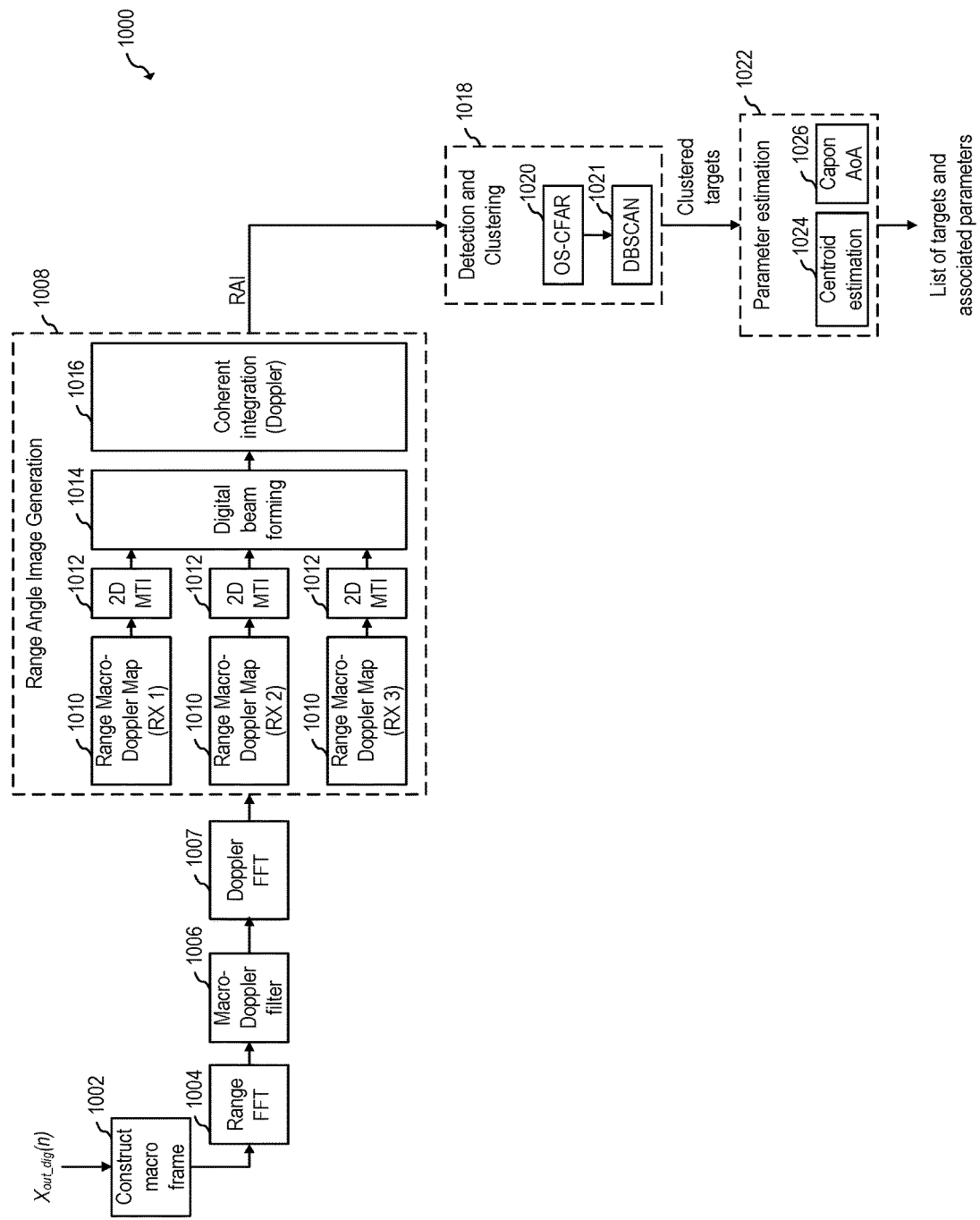
FIG. 10 shows a flow chart of an embodiment method for detecting targets using the macro detection processing chain of FIG. 6, according to an embodiment of the present invention.

FIG. 10 shows a flow chart of embodiment method 1000 for detecting targets using macro detection processing chain 602, according to an embodiment of the present invention. Method 1000 may be implemented by processing system 104.

During step 1002, macro frames (e.g., 702) are constructed based on physical frames. In some embodiments, the macro frames generated during step 702 are a digital version of the physical frames.

During step 1004, a range FFT is performed on the macro frame (e.g., for each receiving channel, e.g., for each receiving antenna 116). For example, in some embodiments, a windowed FFT having a length of a chirp (e.g., 106) is calculated for each of a predetermined number of chirps (e.g., all chirps) in a macro frame. The result of the range FFT is an indication of energy distribution across ranges for each chirp.

During step 1006, macro-Doppler filtering is performed. For example, in some embodiments, a low pass filter is applied to spectrograms produced during step 1004.

During step 1007, a Doppler FFT is performed on the filtered range FFT (e.g., for each receiving antenna 116). For example, in some embodiments, an FFT is calculated across each range bin over a number of consecutive periods to extract Doppler information. The result of step 1005 are range Doppler maps (also known are range-Doppler images or RDIs) for each of the receiving channels (e.g., for each receiving antenna 116).

During step 1008, a range-angle image (RAI) is generated based on the RDIs generated during step 1005. For example, in some embodiments, two-dimensional (2D) MTI filtering is applied to each RDI during step 1012. Digital beamforming is performed during step 1014, in which the angle of arrival is determined by comparing complex numbers from each of the RDIs (e.g., from respective receiving antennas 116). The resulting RAIs are coherently integrated during step 1016.

During step 1018, detection and clustering of potential targets is performed. For example, in some embodiments, an order statistics (OS) constant false alarm rate (CFAR) (OS-CFAR) detector is performed during step 1020. The CFAR detector generates a detection image in which, e.g., "ones" represent targets and "zeros" represent non-targets based, e.g., on the power levels of the range-Doppler image. For example, in some embodiments, the CFAR detector compares the power levels of the RAI with a threshold, and points above the threshold are labeled as targets while points below the threshold are labeled as non-targets. Although targets may be indicated by ones and non-targets may be indicated by zeros, it is understood that other values may be used to indicate targets and non-targets.

Targets present in the detection image are clustered during step 1021 using a density-based spatial clustering of applications with noise (DBSCAN) algorithm to associate targets to clusters. The output of DBSCAN is a grouping (cluster) of the detected points, so that each grouping is associated with a respective target.

During step 1022, parameter estimations for each clustered target (e.g., from step 1018) is generated. For example, during step 1024, an estimation of the centroid of the range of each target cluster is performed (e.g., px and py in Equation 1). During step 1026, angle of arrival (AoA) is estimated for each target. For example, in some embodiments, a minimum variance Distortionless (MVDR) technique, also known as Capon, may be used to determined angle of arrival during step 1026. Other methods may also be used.

In some embodiments, the output of step 1022 is a list of detected targets and associated parameters (e.g., location of centroid, such as range of centroid and angle, Doppler velocity, etc.).

Figure 11:
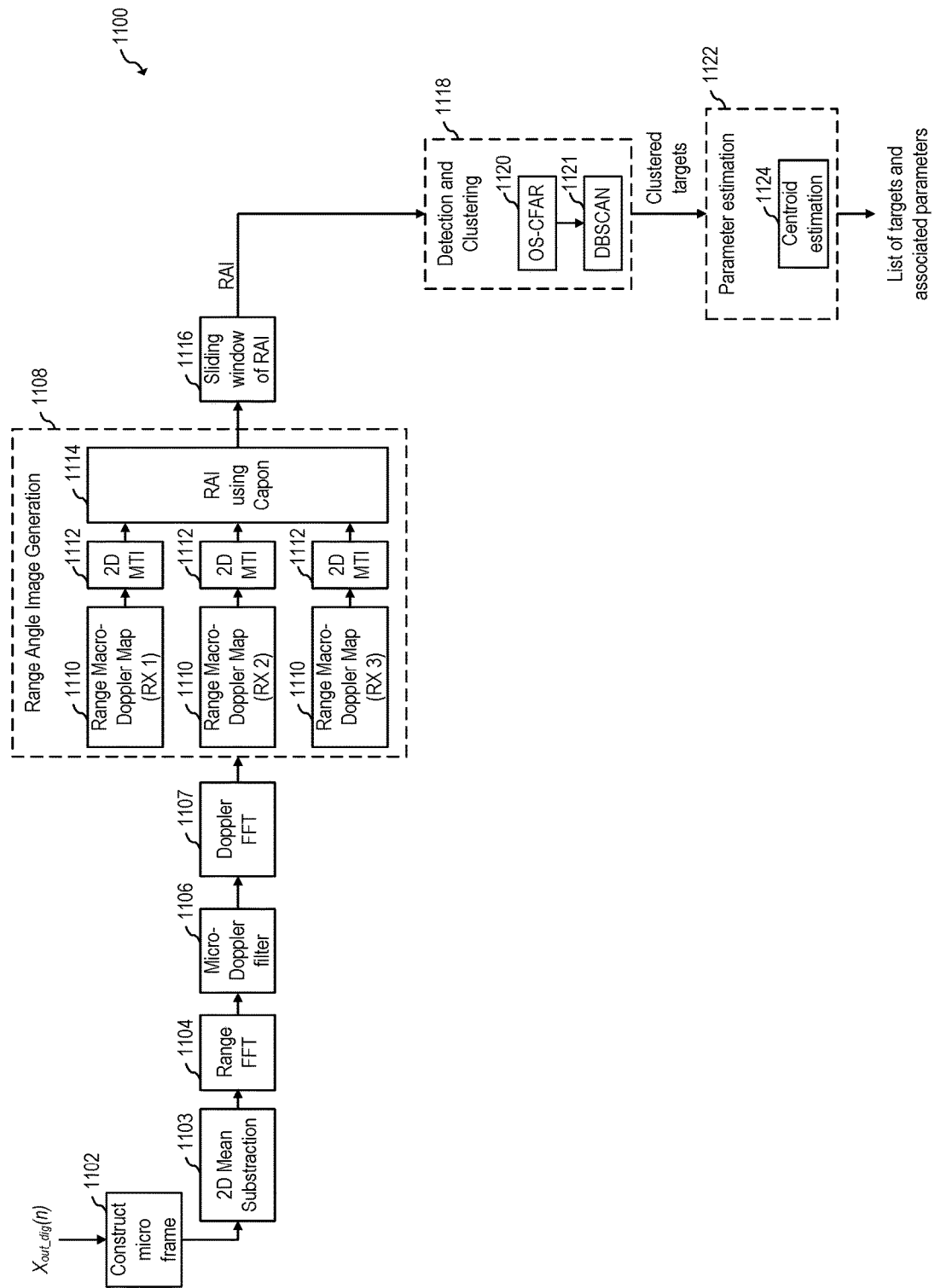
FIGS. 11 and 12 show flow charts of embodiment methods for detecting targets using the micro detection processing chain of FIG. 6, according to embodiments of the present invention.

FIG. 11 shows a flow chart of embodiment method 1100 for detecting targets using micro detection processing chain 604, according to an embodiment of the present invention. Method 1100 may be implemented by processing system 104.

During step 1102, micro frames (e.g., 704) are constructed, e.g., by using methods 800 or 900.

During step 1103, a 2D mean subtraction may be performed on the micro frames.

During step 1104, a range FFT is performed on the micro frame (e.g., for each receiving channel, e.g., for each receiving antenna 116). For example, in some embodiments, a windowed FFT having a length of a chirp (e.g., 106 or 806) is calculated for each of a predetermined number of chirps (e.g., all chirps) in a micro frame. The result of the range FFT is an indication of energy distribution across ranges for each chirp.

During step 1106, micro-Doppler filtering is performed. For example, in some embodiments, a low pass filter is applied to the output of the range FFT. In some embodiments, the cut-off frequency is based on the frequency range of vital signs of the target. For example, in some embodiments, the cut-off frequency of the low pass filter is 5 Hz to allow frequency content associated with heartbeat rate and respiration rate of a static (idle) human. By filtering frequencies outside a human vital sign frequency range, some embodiments, advantageously remove static targets such as walls and chairs, as well as moving targets such as a walking human, while preserving targets that remain static for long enough so that energy content in the vital sign range is captured by the millimeter-wave radar sensor 102 (e.g., a walking or running human, although still having a heartbeat and respiration rate at the vital sign range, may not stay in the same location long enough to trigger detection of the micro detection processing chain 604).

In some embodiments, the low pass filter has a fixed cut-off frequency. In some embodiments, the low-pass filter has a random cut-off frequency. In some embodiments, a random cut-off frequency, e.g., in the range of the vital signs of a human, may advantageously help in removing the frequencies from macro-Doppler motion of target spilled over into micro-Doppler frequency range spuriously. As a result, in some embodiments, a status human is detected even if the cut-off is random, and the macro-Doppler motion targets are removed.

During step 1107 a Doppler FFT is performed on the filtered range FFTs. For example, in some embodiments, an FFT is calculated across each range bin over a number of consecutive periods to extract Doppler information. The result of step 1106 are range-Doppler maps for each of the receiving channels (e.g., for each receiving antenna 116).

During step 1108, a range-angle image (RAI) is generated based on the RDIs generated during step 1107. For example, in some embodiments, 2D MTI filtering is applied to each RDI during step 1112, and the RAI is generated during step 1114 using Capon. In some embodiments, applying MTI filtering during step 1112 advantageously removes information about static targets such as walls and chairs, while preserving information of humans with vital signs (which may have energy content in the frequency range covered by the micro frames, which in some embodiments may be, e.g., between 0.5 Hz and 5 Hz).

During step 1116, a sliding window is applied to the RAIs generated during step 1114. In some embodiments, the integration of the RAIs is performed using mean, geometric mean, or peak-to-average-ratio (PAPR) operations. Other operations may also be used. In some embodiments, applying a sliding window to the RAIs generated during step 1114 advantageously increases the SNR of static targets, such as idle humans, in the RAIs generated during step 1116.

During step 1118, detection and clustering of potential targets is performed. For example, in some embodiments, an OS-CFAR detector is performed during step 1120 to generate a detection image. Targets present in the detection image are clustered during step 1121 using DBSCAN to generate a grouping (cluster) of the detected points, so that each grouping is associated with a respective target.

During step 1122, parameter estimations for each clustered target (e.g., from step 1118) is generated. For example, during step 1124, an estimation of the centroid of the range of each target cluster is performed (e.g., px and py in Equation 1, e.g., after conversion from polar coordinates).

In some embodiments, the output of step 1122 is a list of static (e.g., idle humans) detected targets and associated parameters (e.g., location of centroid, such as range of centroid and angle, etc.).

Figure 12:
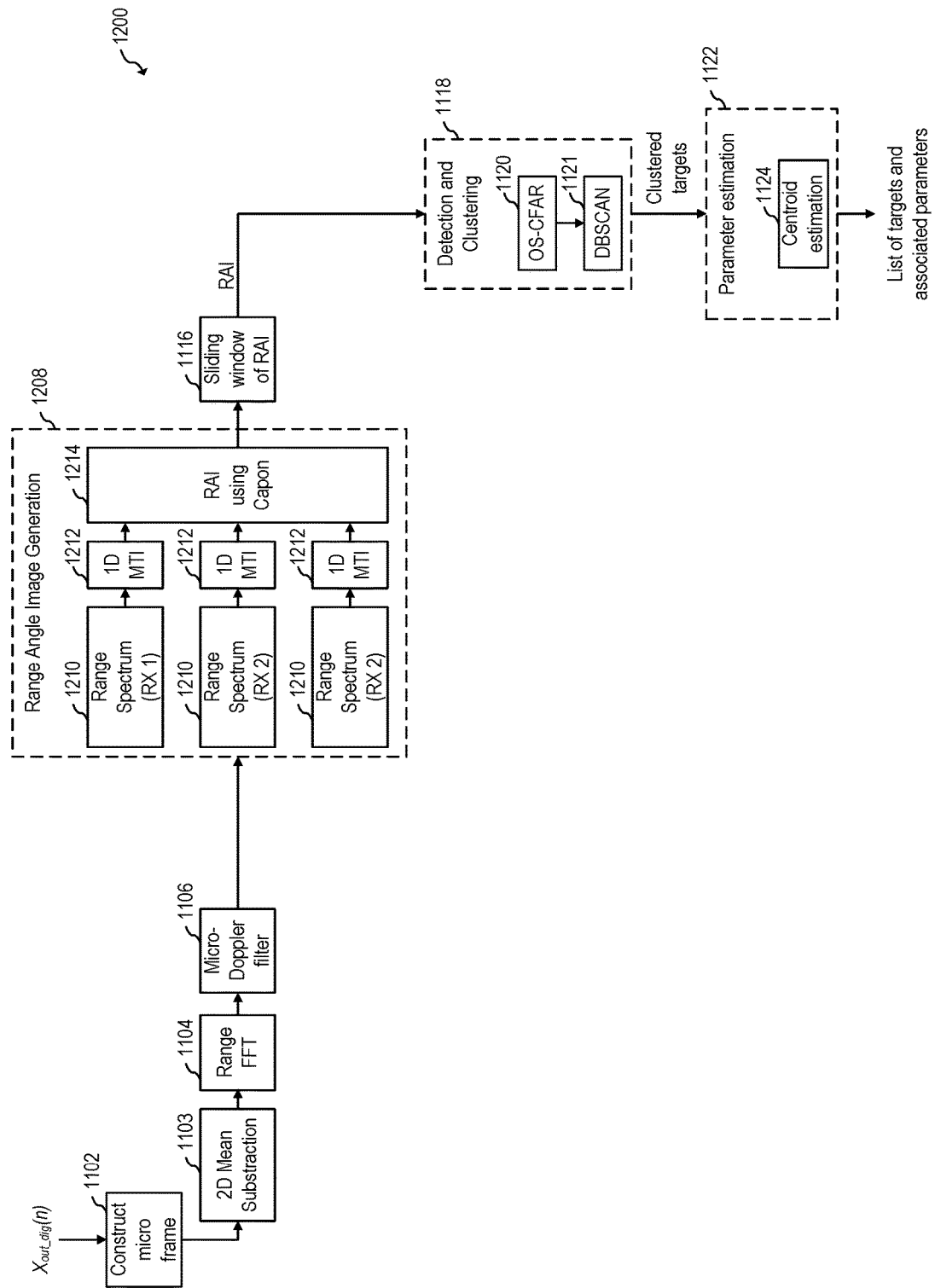

FIG. 12 shows a flow chart of embodiment method 1100 for detecting targets using micro detection processing chain 604, according to an embodiment of the present invention. Method 1200 may be implemented by processing system 104.

Method 1200 includes steps 1102, 1103, 1104, 1106, 1208, 1116, 1118, and 1122. In some embodiments, steps 1102, 1103, 1104, 1106, 1116, 1118, and 1122 may be implemented in a similar manner as in method 1100.

During step 1208, a RAI is generated based on the spectrograms generated during step 1104 (which may be filtered during step 1106). For example, in some embodiments, 1D MTI filtering is applied to each spectrogram during step 1212, and the RAI is generated during step 1214 using Capon. In some embodiments, applying MTI filtering during step 1212 advantageously removes information about static targets such as walls and chairs, while preserving information of humans with vital signs (which may have energy content in the frequency range covered by the micro frames, which in some embodiments may be, e.g., between 0.5 Hz and 5 Hz).

Figure 13:
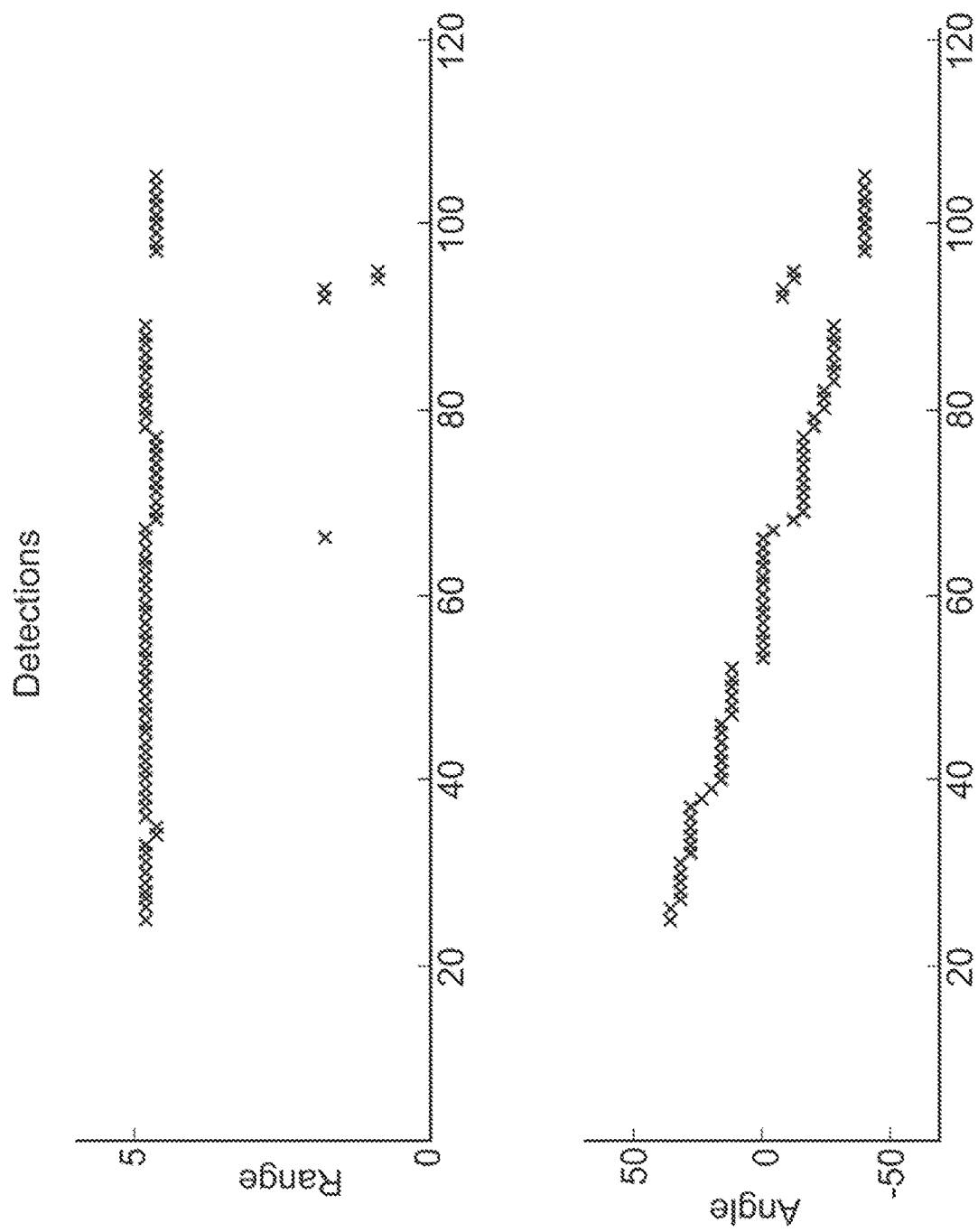
FIG. 13 shows target detection results illustrating range and angle of a detected human target using the micro detection processing chain of FIG. 6, according to an embodiment of the present invention.

FIG. 13 shows target detection results illustrating range and angle of a detected human target using micro detection processing chain 604 implementing method 1100, according to an embodiment of the present invention. In the embodiment illustrated in FIG. 13, each micro frame 704 includes 32 chirps, $T_{micro}$ is 3.2 s, and a sliding window of 8 RAIs is used during step 1116.

As shown in FIG. 13, there is a high probability of detection of a human target that transitions between standing idle and walking radially at about 5 m from millimeter-wave radar sensor 102 from about −40° to about 40°.

In an embodiment of the present invention, a tracker is used to track human targets as the targets transition between a moving state and a static state. A static target model is used to predict the location of a target if the target is/remains static. A moving model is used to predict the location of the target if the target is/remains moving. A model probability is determined, where the model probability is indicative of the likelihood that the target is in the static state or the moving state based on the predicted locations of the static target model and the moving model. The target is associated with a static state or a moving state based on the model probability. In some embodiments, a track is deleted based on the model probability.

Figure 14:
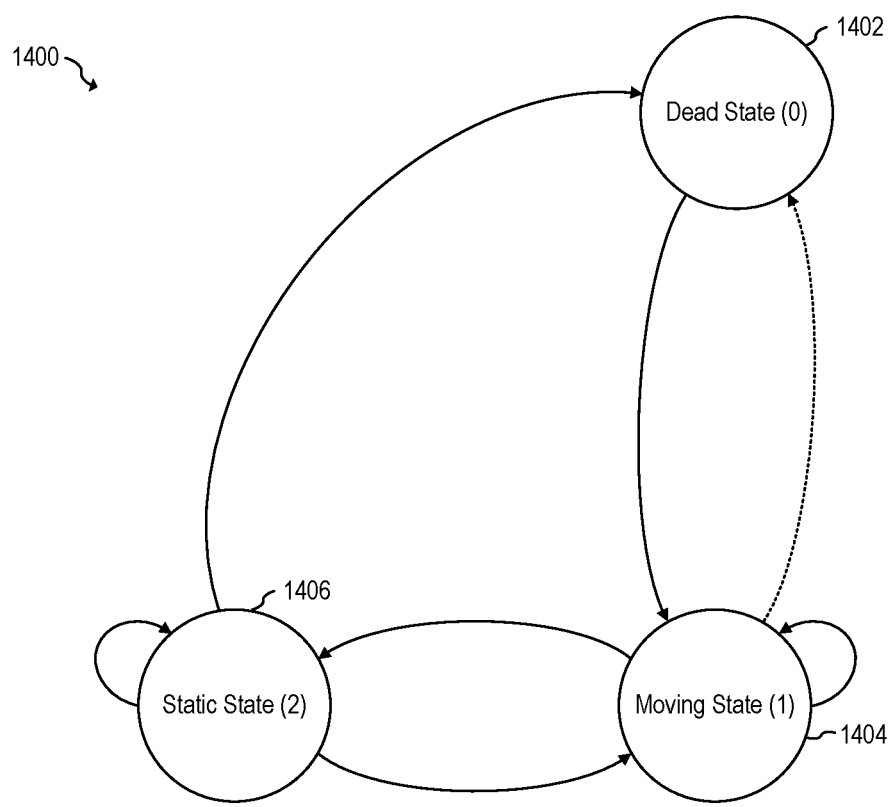
FIG. 14 shows a state diagram for tracking a human target, according to an embodiment of the present invention.

In some embodiments, tracker 608 may be used to track human targets by using a state machine (e.g., implemented by processing system 104). For example, FIG. 14 shows state diagram 1400 for tracking a human target, according to an embodiment of the present invention. State diagram 1400 includes dead state 1402, moving state 1404, and static state 1406. Dead state 1402 is associated with a human target that is not being tracked (e.g., because the corresponding track has been deleted or has not been created). Moving state 1404 is associated with a human target that is moving. Static state 1406 is associated with a human target that is static (e.g., seating, standing idle, or lying in the floor). In some embodiments, other states may be used, such as an unsure state associated with a potential human target (e.g., used before creating a track for the potential human target).

As shown by state diagram 1400, a target transitions into a static state only after being in a moving state. Thus, some embodiments advantageously avoid tracking static objects such as walls even if such objects are detected by micro detection processing chain 604.

As shown by state diagram 1400, a track may be deleted when a target is no longer detected in the static state (e.g., by transitioning from static state 1406 to dead state 1402). In some embodiments, a track is only deleted after tracking a target in the static state (no transition between moving state 1404 and dead state 1402).

In some embodiments, a track may be deleted when a target disappears after being in the moving state without transitioning into the static state. For example, in some embodiments, if a track that is tracking a target does not find a detected moving target from macro detection processing chain 602 (e.g., based on a probabilistic data association filter, also known as PDAF) and also does not find a detected static target from micro detection processing chain 604 (e.g., based on PDAF), a track may be deleted without transitioning into a static state.

When a target is in moving state 1404, tracker 608 may use a coordinated turn model to track the target while the target is/remains in moving state 1404. For example, in some embodiments, tracking of a moving target in moving state 1404 may be performed as $$X = FX + Q \quad (2)$$

where X are the tracked state variables, F is the prediction function, and Q is the covariance matrix. In some embodiments, the state variables X are $$X = [p_x, p_y, v_r, h, w] \quad (3)$$

where $p_x$ and $p_y$ correspond to the location of the centroid of the target in the x-y plane, $v_r$ is the radial velocity, h corresponds to the angle of the target from the millimeter-wave radar sensor 102, and w corresponds to the change in angle h. In some embodiments, the prediction function F may be given as $$F = \begin{bmatrix} p_x + \frac{2v_r}{w} \sin\left(\frac{wT}{2}\right) \cos\left(h + \frac{wT}{2}\right) \\ p_y + \frac{2v_r}{w} \sin\left(\frac{wT}{2}\right) \sin\left(h + \frac{wT}{2}\right) \\ v_r \\ h + wT \\ w \end{bmatrix} \quad (4)$$

where T is the time between tracking samples.

In some embodiments, an unscented Kalman filter is used for non-linear transformations for prediction and measurements of tracked moving targets (while in moving state 1404).

When a target is in static state 1406, tracker 608 may use a static target model to track the target while the target is/remains in static state 1406. For example, in some embodiments, tracking of a static target in static state 1406 may be performed as $$X = X + q \text{ where } q \in N(0, Q) \quad (5)$$

where X are the tracked state variables, q is an uncertainty value. In some embodiments, the state variables X are $$X = [p_x, p_y] \quad (6)$$

where $p_x$ and $p_y$ correspond to the location of the centroid of the target in the x-y plane. I In some embodiments, tracker 608 may use polar coordinates for tracking a static target while the static target is in static state 1406. The measurements in polar coordinate form (e.g., range, angle, and velocity) may be available from millimeter-wave radar sensor 102. The relationship between the polar coordinate and Cartesian coordinate systems may be given by $$r = \sqrt{(p_x^2 + p_y^2)} \quad \theta = \tan\left(\frac{p_y}{p_x}\right) \quad v_r = 0 \quad (7)$$

where r corresponds to the range from millimeter-wave radar sensor 102, θ corresponds to the angle of the target from millimeter-wave radar sensor 102, and the radial velocity vr is 0 (since the target is static).

In some embodiments, tracker 608 may calculate the predicted polar coordinates by $$Z = h(X) \quad (8)$$

where h(X) is a non-linear transformation from Cartesian coordinates to polar coordinates. In some embodiments, h(X) may be implemented with an unscented transform, e.g., to better estimate the non-linearities associated with the transformation. The unscented transform may be implemented in any way known in the art. For example, it may be easier to approximate a probability distribution that to approximate an arbitrary non-linear function or transformation. Thus, if y=g(x) and x~N ($\hat{x}$, P), p(y) may be approximated by $$E\{y\} \approx \mu_y = \sum_{i=0}^{N} W_i g(\chi^{(i)}) \quad (9)$$

$$\text{Cov}\{y\} \approx \sum_{i=0}^{N} W_i (g(\chi^{(i)}) - \mu_y)(g(\chi^{(i)}) - \mu_y)^T$$

where $\chi^{(i)}$ are σ-points and $W_i$ are the associated weights. The unscented transform may be performed by forming a set of 2n+1 σ-points as follows:

$$\chi^{(0)} = \hat{x} \quad (10)$$

$$\chi^{(i)} = \hat{x} + \sqrt{\frac{n}{1 - W_0}} P_i^{\frac{1}{2}}, i = 1, 2, \ldots, n,$$

$$\chi^{(i+n)} = \hat{x} - \sqrt{\frac{n}{1 - W_0}} P_i^{\frac{1}{2}}, i = 1, 2, \ldots, n,$$

$$W_i = \frac{1 - W_0}{2n}$$

where $$P_i^{\frac{1}{2}}$$

is the ith column of $$P^{\frac{1}{2}}$$

and P is the covariance matrix for state vector X (thus, in some embodiments, $$P^{\frac{1}{2}}$$

is the lower triangular values of the Cholesky decomposition of the P matrix). If x is Gaussian, $$W_0 = 1 - \frac{n}{3}.$$

As illustrated by Equation 5, in some embodiments, the static target model makes a prediction of a same location but adding uncertainty (e.g., noise) around the location. By adding noise to the static prediction, some embodiments advantageously are capable of correctly predict and continue to track static targets that may appear to move slightly, e.g., because of noise in the measurement, noise in the radar system, or actual slight movement (e.g., when an idle human moves the hands, shifts weight from left foot to right foot, etc.).

In some embodiments, tracker 608 determines the state of a tracked target (e.g., moving state 1404 or static state 1406), based on inputs from macro detection processing chain 602 and micro detection processing chain 604. For example, FIG. 15 shows transition model 1500 for transitioning between states 1404 and 1406, according to an embodiment of the present invention.

Figure 15:
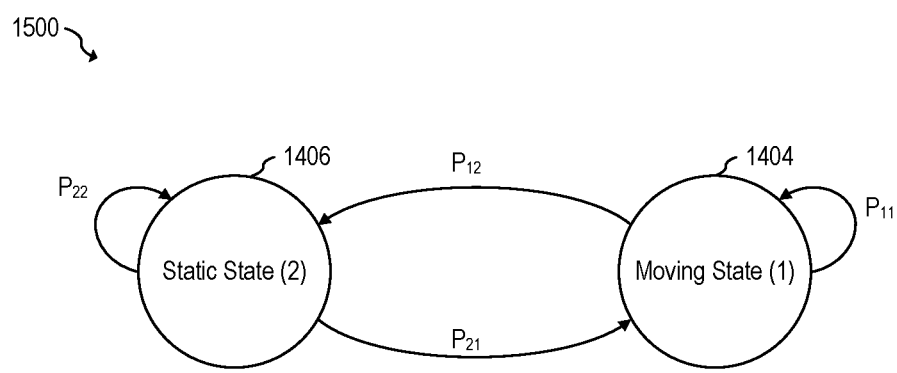
FIG. 15 shows a model for transitioning between states of the state diagram of FIG. 14, according to an embodiment of the present invention.

As shown in FIG. 15, tracker 608 may determine the state of the target based on probability P. For example, if the tracked target is in moving state 1404, $P_{11}$ is 80% and $P_{12}$ is 20%, tracker 608 may determine that the tracked target remains in moving state 1404. If the tracked target is in moving state 1404, $P_{11}$ is 20% and $P_{12}$ is 80%, tracker 608 may determine that the tracked target transitions from moving state 1404 into static state 1406. If the tracked target is in static state 1406, $P_{22}$ is 80% and $P_{21}$ is 20%, tracker 608 may determine that the tracked target remains in static state 1406. If the tracked target is in static state 1406, $P_{22}$ is 20% and $P_{21}$ is 80%, tracker 608 may determine that the tracked target transitions from static state 1406 into static state 1404.

In some embodiments, a model probability L is determined for the motion model (used for moving state 1404) and static target model (used for static state 1406). Probabilities $P_{11}$, $P_{12}$, $P_{21}$, and $P_{22}$ are based on the current state of the target and the model probability L (e.g., may be the normalized versions of L). For example, in some embodiments, model probabilities $L_{static}$ and $L_{motion}$, corresponding to the static target model and motion model, respectively, are determine by computing the Mahalanobis distance, e.g., as $$L_{static} = \begin{pmatrix} (z - Z_s)S^{-1}(z - Z_s)^T \\ (z_{s\_hist} - Z_{s\_hist})(z_{s\_hist} - Z_{s\_hist})^T \end{pmatrix} \quad (11)$$

$$L_{motion} = \begin{pmatrix} (z - Z_m)S^{-1}(z - Z_m)^T \\ (z_{m\_hist} - Z_{m\_hist})(z_{m\_hist} - Z_{m\_hist})^T \end{pmatrix} \quad (12)$$

where S is the covariances between z and $Z_s$ (which may be defined by the Mahalanobis distance), z corresponds to the measured target location, $Z_s$ corresponds to the predicted target location according to the static target model, $z_{s\_hist}$ corresponds to the history (e.g., last b micro frames, where b is a positive integer greater than 1, such as 5, 6, or more) of measured target locations, $Z_{s\_hist}$ corresponds to the history (e.g., last b micro frames) of predicted target locations according to the static target model, $Z_m$ corresponds to the predicted target location according to the motion model, $z_{m\_hist}$ corresponds to the history (e.g., last b macro frames) of measured target locations, and $Z_{m\_hist}$ corresponds to the history (e.g., last b macro frames) of predicted target locations according to the motion model.

Figure 16:
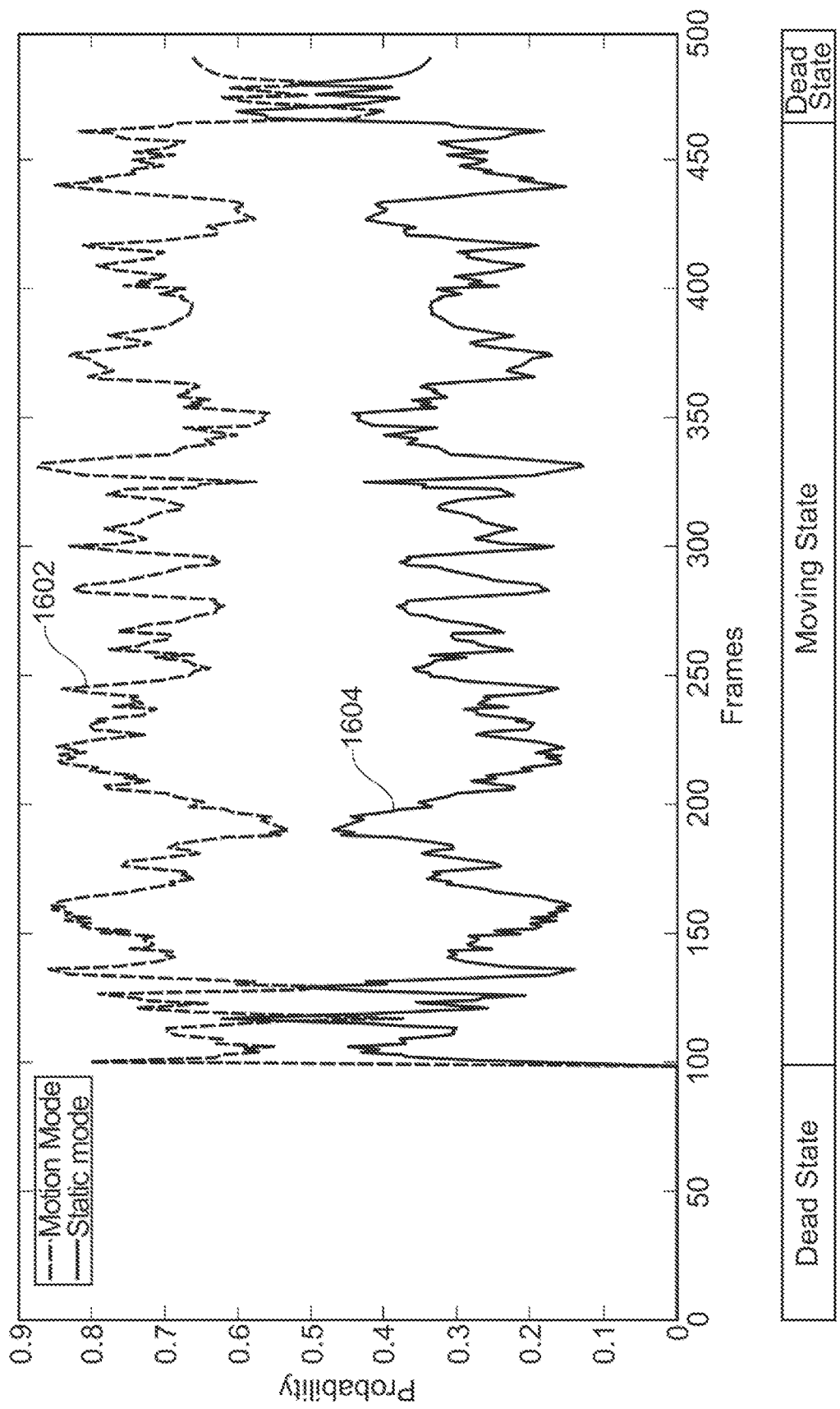
FIG. 16 shows normalized model probabilities for a tracked human target, according to an embodiment of the present invention.

FIG. 16 shows normalized model probabilities for a tracked human target, according to an embodiment of the present invention. Curves 1602 and 1604 correspond to normalized motion model probability ($\mu_{motion}$) and static target model probability ($\mu_{static}$), respectively, of a human target that walks at various speeds between physical frames about 100 to about 460).

Figure 17:
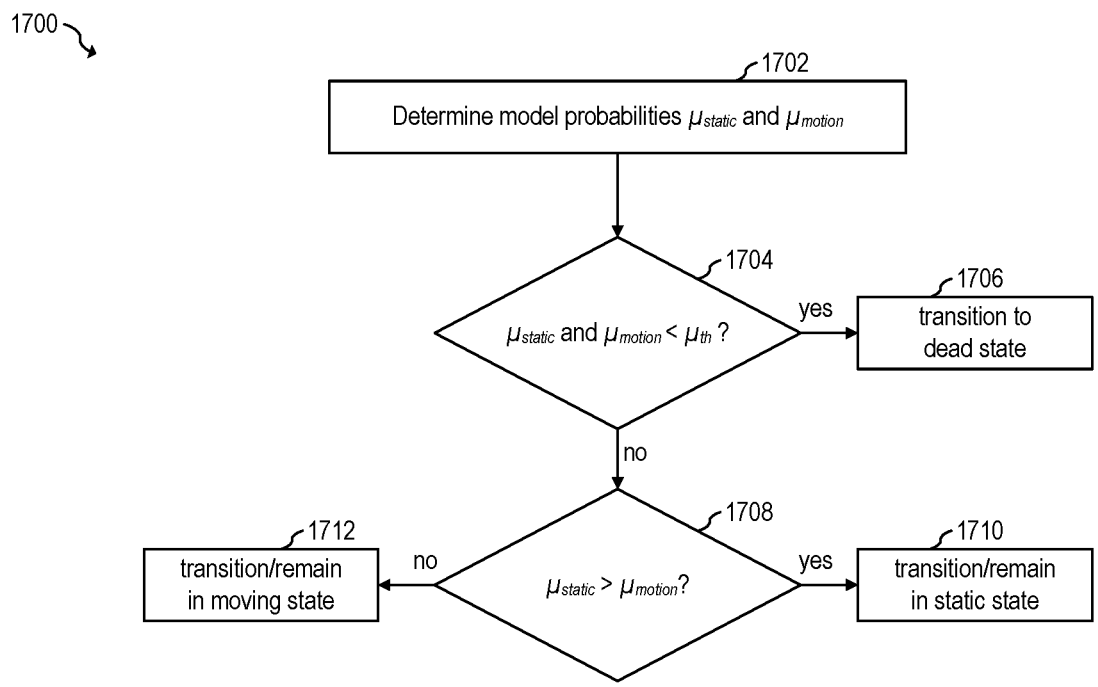
FIG. 17 shows a flow chart of an embodiment method for determining a target state, according to an embodiment of the present invention.

As shown in FIG. 16, the probability of the motion model ($\mu_{motion}$) is higher than the probability of the static target model ($\mu_{static}$). In some embodiments, tracker 608 determines that the state of the target based on which model probability is higher. If both model probabilities are lower than a threshold (e.g., 0.67), them the track is deleted and the target is transitioned into the dead state 1402. For example, FIG. 17 shows a flow chart of embodiment method 1700 for determining a target state, according to an embodiment of the present invention. Method 1700 may be implemented by tracker 608 (e.g., by processing system 104).

During step 1702, normalized model probabilities $\mu_{motion}$ and $\mu_{static}$ are determined. For example, in some embodiments, normalized model probabilities $\mu_{motion}$ and $\mu_{static}$ are determined by calculating model probabilities $L_{static}$ and $L_{motion}$ using equations 11 and 12, respectively, and then normalizing them so that $\mu_{motion} + \mu_{static} = 1$.

During step 1704, normalized model probabilities $\mu_{motion}$ and $\mu_{static}$ are compared with a threshold $\mu_{th}$. If it is determined during step 1704 that both $\mu_{motion}$ and $\mu_{static}$ are lower than the threshold $\mu_{th}$, then a tracker, such as tracker 608, determines that a target is not present and may delete the track during step 1706. Otherwise, the target transitions to the state having the higher model probability, as shown by steps 1708, 1710 and 1712.

In some embodiments, threshold $\mu_{th}$ is 0.67. Other values may also be used. For example, in some embodiments, threshold $\mu_{th}$ is between 0.5 and 0.67. Values higher than 0.67, such as 0.68, 0.69, or higher, may also be used.

In some embodiments, steps 1704 (and therefore 1706) may be omitted.

In some embodiments, a track may be deleted when the tracker (e.g., 608) fails to detect a target for a number of frames. For example, it is possible that noise or other artifacts may cause failure to detect a target during one or a few frames when the target is actually present in the field of view of the millimeter-wave radar sensor 102. To avoid deleting a track when the associated target is still present in the field of view of the millimeter-wave radar sensor 102, some embodiments only delete a track if the target is not detected for d frames, where d is a positive integer greater than 1, such as 3, 5, or more. In some embodiments, a counter is used to count the number of frames without successfully detecting a target associated with a track, and the counter is reset each time the track is successfully associated with a detected target.

In some embodiments, macro detection processing chain 602 and micro detection processing chain 604 operate at different rates. Thus, in some embodiments, targets in moving state 1404 are deleted (transitioned into dead state 1402) after $d_{moving}$ frames, and targets in static state 1406 are deleted (transitioned into dead state 1402) after $d_{static}$ frames, where $d_{moving}$ is greater than $d_{static}$. For example, in some embodiments, $d_{moving} \geq \alpha \cdot d_{static}$, where $\alpha$ is a positive number greater than 1, and where $T_{micro}$ is equal to $\alpha$ times $T_{macro}$. For example, in some embodiments, $d_{moving} \geq P \cdot d_{static}$, where $T_{micro}$ is equal to P times $T_{macro}$. For example, in some embodiments, P is equal to 32 so that $T_{micro}$ is 32 times $T_{macro}$. In such embodiment, $d_{moving}$ may be, e.g., 40 times $d_{static}$.

Figure 18:
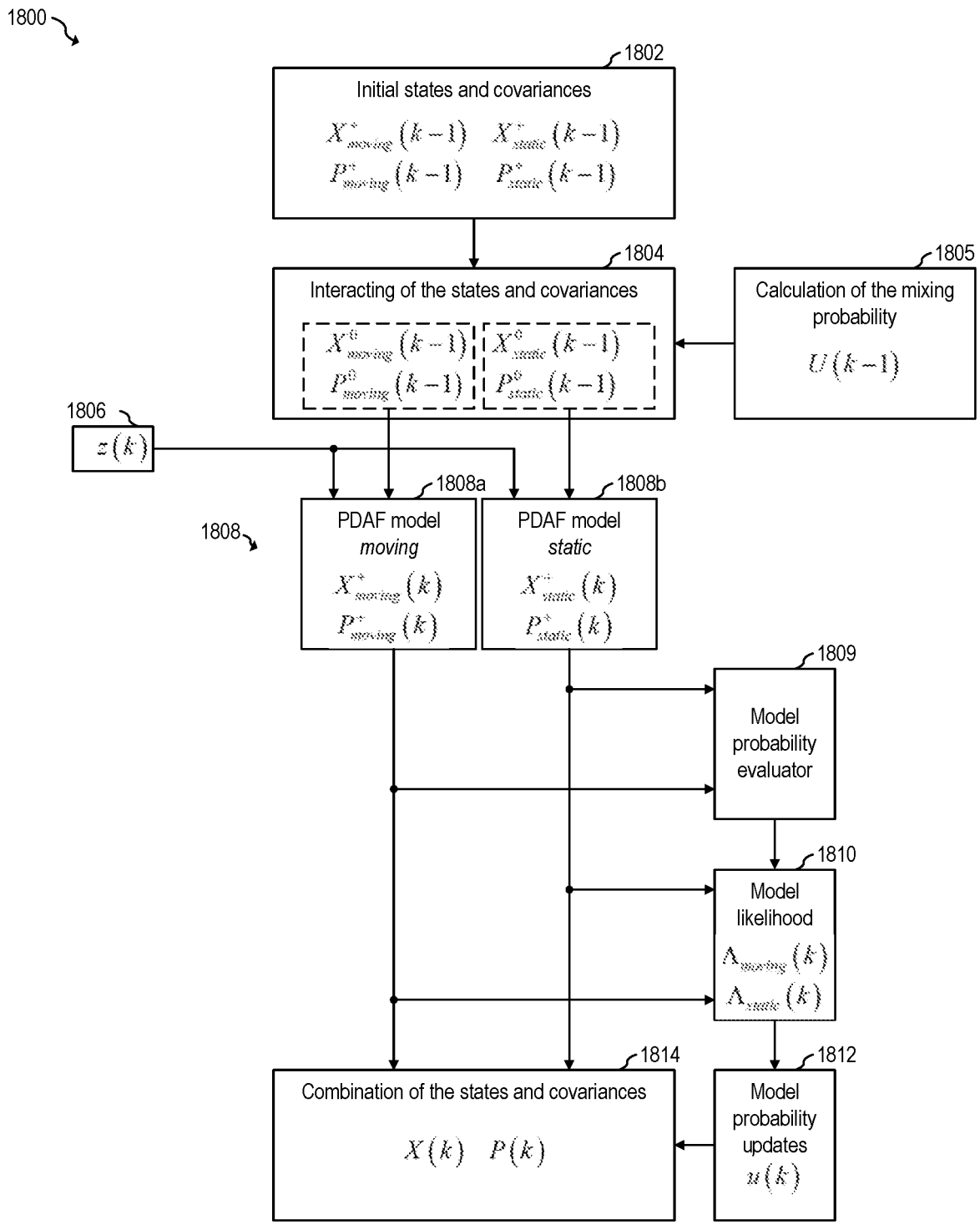
FIG. 18 shows a possible implementation of the tracker of FIG. 6, according to an embodiment of the present invention.

FIG. 18 shows tracker 1800, according to an embodiment of the present invention. Tracker 608 may be implemented as tracker 1800. Tracker 1800 is an IMM tracker.

As shown, tracker 1800 uses an IMM filter in combination with probabilistic data association filter (PDAF) to carry out track filtering and data association for the targets, e.g., as shown by steps 1802, 1804, 1805, 1806, 1808, 1809, 1810, 1812, and 1814.

During step 1802, the motion model (used for moving state 1404) and static target model (used for static state 1406) are initialized for time step k−1.

During step 1804, the motion model and static target model generate respective prediction for detected targets. In some embodiments, the predictions for detected targets are generated based on mixed probability U(k−1) determined during step 1805. In some embodiments, the mixing of probabilities (e.g., such as using a weighted average) advantageously help in the transition phase between static state 1406 (e.g., using the static target model) and moving state 1404 (e.g., using the motion model).

During step 1806, measurements of detected target(s) (e.g., location information) are performed/received.

During step 1808, PDAF models are used to associate detected targets to tracks. As shown by steps 1802a and 1808b, the motion model, and the static target model generate respective target associations to tracks for the same target(s). For example, in some embodiments, the moving model and the static target model are evaluated independently during step 1808 to generate target association to tracks.

During step 1809, the probability that a particular model (moving model or static target model) is best suited for the current time step k is evaluated for each of the tracked targets. For example, during step 1809, model probabilities $L_{static}$ and $L_{motion}$, are computed, e.g., using Equations 11 and 12. In some embodiments, the normalized model probabilities $\mu_{motion}$ and $\mu_{static}$ are also computed during step 1809.

During step 1810, the model likelihood is evaluated (e.g., using method 1700), e.g., based on the outputs of the PDAF models (determined during steps 1808a and 1808b), which provide the likelihood of each model with respect to the incoming measurement (determined during step 1806).

During step 1812 and based on the results from step 1810, the model probabilities are updated (e.g., based on the result of method 1700), and the detected targets assigned a state (static or moving) during step based on the model probabilities (e.g., using transition model 1500).

During step 1814, the state X and covariances P are updated based on the outputs of steps 1812 and 1808. For example, if the state of a target is associated with the moving state during step 1812, then $X(k) = X_{moving}^+(k)$ $P(k) = P_{moving}^+(k)$.

Otherwise, if the state of a target is associated with the static state during step 1812, then $X(k) = X_{static}^+(k)$ $P(k) = P_{static}^+(k)$.

In some embodiments, macro detection processing chain 602 and micro detection processing chain 604 operate at different rates. Thus, in some embodiments, the detection rates associated with the motion model and the static target model are difference. Thus, in some embodiments, the IMM algorithm advantageously allows for combining state hypotheses from the motion model and the static target model to better estimate the state of the targets witch changing dynamics. A Markov chain associated with the IMM tracker helps to manage the changing dynamics of the targets efficiently. Thus, some embodiments advantageously achieve better and cleaner track handling for multi target scenarios. Some embodiments are advantageously capable of dealing with targets with multiple dynamics more efficiently. Some embodiments are advantageously used for combining data arriving at difference sampling intervals.

In some embodiments, tracker 608 the period between time steps k is equal to $T_{macro}$.

Figure 19:
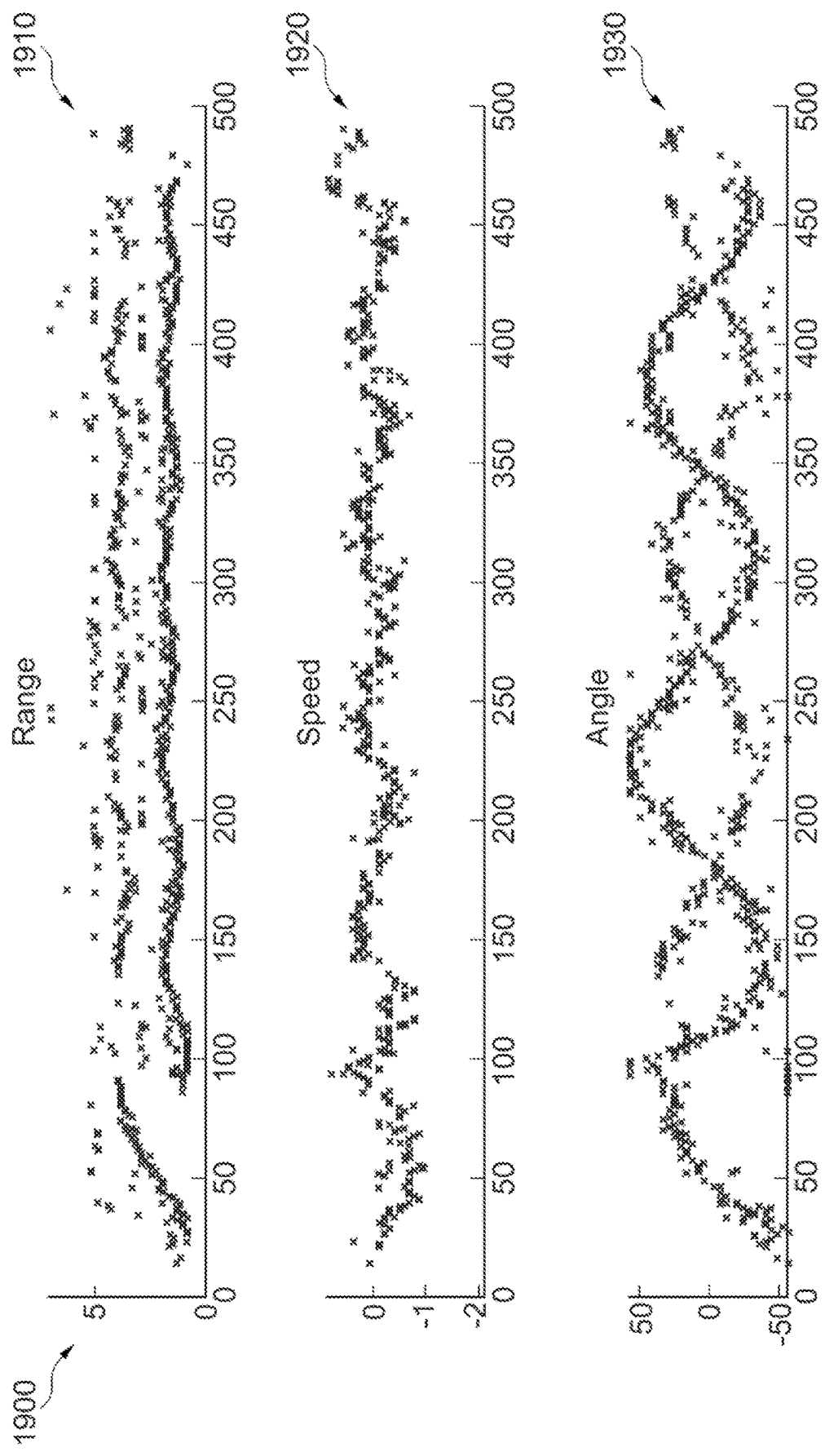
FIGS. 19 and 20 show detection and tracking curves, respectively, of two human targets using the tracker of FIG. 6, according to an embodiment of the present invention.
Figure 20:
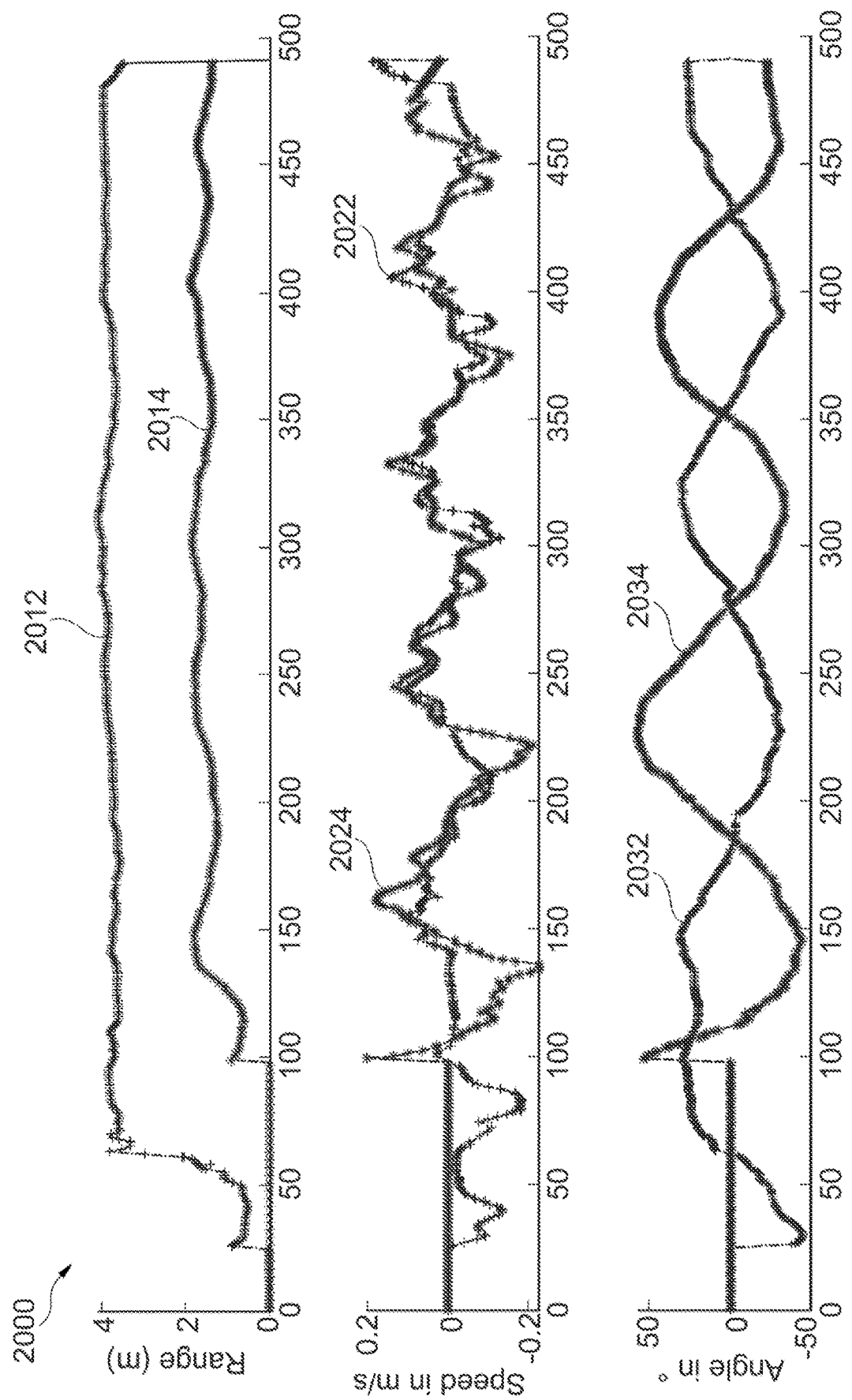

FIGS. 19 and 20 show detection curves 1900 and tracking curves 2000, respectively, of two human targets walking at various speeds using tracker 608, according to an embodiment of the present invention. Curves 2000 may be understood in view of curves 1900.

Curves 2000 represent tracked targets based on the target detections illustrated by curves 1900. Curves 2012, 2022, and 2032 correspond to range, speed, and angle, respectively, of a first human target tracked by tracker 608, and curves 2014, 2024, and 2034 correspond to range, speed, and angle, respectively, of a second human target tracked by tracker 608.

As illustrated by curves 2012, 2022, and 2032, the first human initially moves away from the millimeter-wave radar sensor 102 and, beginning at about frame 60, remains at about the same distance (about 4 m) from millimeter-wave radar sensor 102, and moves at various speed between about −50° to about 50° until disappearing from the field of view of millimeter-wave radar 102 at about frame 490.

As illustrated by curves 2014, 2024, and 2034, the first human initially moves away from the millimeter-wave radar sensor 102 and, beginning at about frame 98, remains at about the same distance (about 1.5 m) from millimeter-wave radar sensor 102, and moves at various speed between about −50° to about 50° until disappearing from the field of view of millimeter-wave radar 102 at about frame 490.

As can be seen from FIGS. 19 and 20, tracker 608 is advantageously capable of keeping alive the track associated to the first human, even as target detection for the first human exhibits various frames without accurate target detection (e.g., as illustrated by curves 1910 between frames about 90 to about 490).

FIGS. 19 and 20 also illustrates that tracker 608 is advantageously capable of distinguishing between the first and second humans and creates a second track at about frame 98 instead of associating the target detections of the second human to the track of the first human.

Example embodiments of the present invention are summarized here. Other embodiments can also be understood from the entirety of the specification and the claims filed herein.

Example 1. A method for tracking a target, the method including: receiving raw data from a millimeter-wave radar, the raw data including a plurality of macro-Doppler frames, each macro-Doppler frame having N chirps, N being a positive integer greater than 1, where each macro-Doppler frame stretches over a time interval having a first duration; generating micro-Doppler frames from the plurality of macro-Doppler frames, each micro-Doppler frame including L chirps from M macro-Doppler frames, M being a positive integer greater than 1, L being a positive integer greater than 1, where each micro-Doppler frame stretches over a time interval having a second duration that is longer than the first duration; detecting one or more moving targets based on the macro-Doppler frames; detecting one or more static targets based on the micro-Doppler frames; and tracking a first target as the target transitions from being detected based on the macro-Doppler frames to being detected based on the micro-Doppler frames.

Example 2. The method of example 1, where tracking the first target includes tracking the first target using an interactive multiple model (IMM).

Example 3. The method of one of examples 1 or 2, where the first target is in a first region, and where tracking the first target includes: determining a first modal probability that a detected moving target in the first region is moving; determining a second modal probability that a detected static target in the first region is static; when the first modal probability is higher than the second modal probability, associating the first target to a moving state, the first target being tracked by a first track; and when the second modal probability is higher than the first modal probability, associating the first target to a static state.

Example 4. The method of one of examples 1 to 3, where tracking the first target further includes: when the first modal probability is below a first threshold, and the second modal probability is below the first threshold, deleting the first track.

Example 5. The method of one of examples 1 to 4, where tracking the first target further includes: deleting the first track when the first target is in the moving state and the first target is not detected for Q frames, Q being a positive integer greater than 1; and deleting the first track when the first target is in the static state and the first target is not detected for P frames, P being a positive integer greater than Q.

Example 6. The method of one of examples 1 to 5, where P is equal to L times Q.

Example 7. The method of one of examples 1 to 6, where L is equal to M, and where generating the L chirps of each micro-Doppler frame includes integrating all chirps of each of M consecutive macro-Doppler frames to generate M integrated chirps, where each micro-Doppler frame includes respective M integrated chirps.

Example 8. The method of one of examples 1 to 7, where L is equal to M, and where generating the L chirps of each micro-Doppler frame includes selecting a chirp from each of M consecutive macro-Doppler frames to generate M selected chirps, where each micro-Doppler frame includes respective M selected chirps.

Example 9. The method of one of examples 1 to 8, where the second duration is selected to allow the micro-Doppler frames to include vital sign content of the one or more static targets.

Example 10. The method of one of examples 1 to 9, where the vital sign content includes heartbeat rate or respiration rate.

Example 11. The method of one of examples 1 to 10, further including filtering data of the micro-Doppler frames to remove low frequency content and allow content between 0.5 Hz and 5 Hz.

Example 12. The method of one of examples 1 to 11, where detecting the one or more static targets includes: performing a range Fourier transform based on the micro-Doppler frames to generate micro-Doppler frame range data; generating micro range angle images (RAIs) based on micro-Doppler frame range data; and detecting a static target based on the generated micro RAIs.

Example 13. The method of one of examples 1 to 12, where detecting the one or more static targets further includes performing a sliding window on the generated micro RAIs to generate integrated micro RAIs, and where detecting the static target is based on the integrated micro RAIs.

Example 14. The method of one of examples 1 to 13, where detecting the one or more static targets further includes low-pass filtering the micro-Doppler frame range data, where generating the micro RAIs is based on the low-pass filtered micro-Doppler frame range data.

Example 15. The method of one of examples 1 to 14, where low-pass filtering the micro-Doppler frame range data includes low-pass filtering the micro-Doppler frame range data with a random cut-off frequency.

Example 16. The method of one of examples 1 to 15, where low-pass filtering the micro-Doppler frame range data includes low-pass filtering the micro-Doppler frame range data with a fixed cut-off frequency.

Example 17. The method of one of examples 1 to 16, where generating the micro RAIs includes: generating a range-Doppler map; performing a two-dimensional (2D) moving target indication (MTI) filter on the range-Doppler map to generate a filtered range-Doppler map; and generating the micro RAIs based on the filtered range-Doppler map.

Example 18. The method of one of examples 1 to 17, where generating the micro RAIs includes: generating a range spectrum; performing a one-dimensional (1D) moving target indication (MTI) filter on the range spectrum to generate a filtered range-Doppler map; and generating the micro RAIs based on the filtered range-Doppler map.

Example 19. The method of one of examples 1 to 18, where detecting the one or more moving targets includes: performing a range Fourier transform based on the macro-Doppler frames to generate macro frame range data; generating macro range angle images (RAIs) based on macro-Doppler frame range data; and detecting a moving target based on the generated macro RAIs.

Example 20. The method of one of examples 1 to 19, where L is equal to 32 and the second duration is about 3.2 seconds.

Example 21. The method of one of examples 1 to 20, where the first target is a human target.

Example 22. A method including: receiving raw data from a millimeter-wave radar, the raw data including a plurality of macro-Doppler frames, each macro-Doppler frame having N chirps, N being a positive integer greater than 1, where each macro-Doppler frame stretches over a time interval having a first duration; generating micro-Doppler frames from the plurality of macro-Doppler frames, each micro-Doppler frame including L chirps from M macro-Doppler frames, M being a positive integer greater than 1, L being a positive integer greater than 1, where each micro-Doppler frame stretches over a time interval having a second duration that is longer than the first duration; detecting one or more moving targets based on the macro-Doppler frames; and detecting one or more static targets based on the micro-Doppler frames, where the second duration is selected to allow the micro-Doppler frames to include vital sign content of the one or more static targets.

Example 23. The method of example 22, further including tracking a first target with a first track as the first target transitions from being detected based on the macro-Doppler frames to being detected based on the micro-Doppler frames.

Example 24. A millimeter-wave radar including: a transmitting antenna; a plurality of receiving antennas; a radar sensor configured to: transmit radar signals using the transmitting antenna, and receive reflected radar signals using the plurality of receiving antennas; and a processor configured to: receive raw data from the radar sensor, the raw data including a plurality of macro-Doppler frames, each macro-Doppler frame having N chirps, N being a positive integer greater than 1, where each macro-Doppler frame stretches over a time interval having a first duration, generate micro-Doppler frames from the plurality of macro-Doppler frames, each micro-Doppler frame including L chirps from M macro-Doppler frames, M being a positive integer greater than 1, L being a positive integer greater than 1, where each micro-Doppler frame stretches over a time interval having a second duration that is longer than the first duration; detect one or more moving targets based on the macro-Doppler frames; detect one or more static targets based on the micro-Doppler frames; and track a first target as the first target transitions from being detected based on the macro-Doppler frames to being detected based on the micro-Doppler frames.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for tracking a target, the method comprising:
   receiving raw data from a millimeter-wave radar, the raw data comprising a plurality of macro-Doppler frames, each macro-Doppler frame having N chirps, N being a positive integer greater than 1, wherein each macro-Doppler frame stretches over a time interval having a first duration;
   generating micro-Doppler frames from the plurality of macro-Doppler frames, each micro-Doppler frame comprising L chirps from M macro-Doppler frames, M being a positive integer greater than 1, L being a positive integer greater than 1, wherein each micro-Doppler frame stretches over a time interval having a second duration that is longer than the first duration;
   detecting one or more moving targets based on the macro-Doppler frames;
   detecting one or more static targets based on the micro-Doppler frames;
   determining whether a first target of the one or more moving targets detected based on the macro-Doppler frames stops moving; and
   tracking the first target using the micro-Doppler frames only after the first target stops moving based on the determining.

2. The method of claim 1, wherein tracking the first target comprises tracking the first target using an interactive multiple model (IMM).

3. The method of claim 1, wherein the first target is in a first region, and wherein tracking the first target comprises:
   determining a first modal probability that a detected moving target in the first region is moving;
   determining a second modal probability that a detected static target in the first region is static;
   in response to the first modal probability being higher than the second modal probability, associating the first target to a moving state, the first target being tracked by a first track; and
   in response to the second modal probability being higher than the first modal probability, associating the first target to a static state.

4. The method of claim 3, wherein tracking the first target further comprises:
   when the first modal probability is below a first threshold, and the second modal probability is below the first threshold, deleting the first track.

5. The method of claim 3, wherein tracking the first target further comprises:
   deleting the first track in response to the first target being in the moving state and the first target is not detected for Q frames, Q being a positive integer greater than 1; and
   deleting the first track in response to the first target being in the static state and the first target is not detected for P frames, P being a positive integer greater than Q.

6. The method of claim 5, wherein P is equal to L times Q.

7. The method of claim 1, wherein L is equal to M, and wherein generating the L chirps of each micro-Doppler frame comprises integrating all chirps of each of M consecutive macro-Doppler frames to generate M integrated chirps, wherein each micro-Doppler frame comprises respective M integrated chirps.

8. The method of claim 1, wherein L is equal to M, and wherein generating the L chirps of each micro-Doppler frame comprises selecting a chirp from each of M consecutive macro-Doppler frames to generate M selected chirps, wherein each micro-Doppler frame comprises respective M selected chirps.

9. The method of claim 1, wherein the second duration is selected to allow the micro-Doppler frames to include vital sign content of the one or more static targets.

10. The method of claim 9, wherein the vital sign content comprises heartbeat rate or respiration rate.

11. The method of claim 1, further comprising filtering data of the micro-Doppler frames to remove low frequency content and allow content between 0.5 Hz and 5 Hz.

12. The method of claim 1, wherein detecting the one or more static targets comprises:
   performing a range Fourier transform based on the micro-Doppler frames to generate micro-Doppler frame range data;
   generating micro range angle images (RAIs) based on micro-Doppler frame range data; and
   detecting the one or more static targets based on the generated micro RAIs.

13. The method of claim 12, wherein detecting the one or more static targets further comprises performing a sliding window on the generated micro RAIs to generate integrated micro RAIs, and wherein detecting the static target is based on the integrated micro RAIs.

14. The method of claim 12, wherein detecting the one or more static targets further comprises low-pass filtering the micro-Doppler frame range data, wherein generating the micro RAIs is based on the low-pass filtered micro-Doppler frame range data.

15. The method of claim 14, wherein low-pass filtering the micro-Doppler frame range data comprises low-pass filtering the micro-Doppler frame range data with a randomly selected cut-off frequency.

16. The method of claim 14, wherein low-pass filtering the micro-Doppler frame range data comprises low-pass filtering the micro-Doppler frame range data with a fixed cut-off frequency.

17. The method of claim 12, wherein generating the micro RAIs comprises:
generating a range-Doppler map;
performing a two-dimensional (2D) moving target indication (MTI) filter on the range-Doppler map to generate a filtered range-Doppler map; and
generating the micro RAIs based on the filtered range-Doppler map.

18. The method of claim 12, wherein generating the micro RAIs comprises:
generating a range spectrum;
performing a one-dimensional (1D) moving target indication (MTI) filter on the range spectrum to generate a filtered range-Doppler map; and
generating the micro RAIs based on the filtered range-Doppler map.

19. The method of claim 12, wherein detecting the one or more moving targets comprises:
performing a range Fourier transform based on the macro-Doppler frames to generate macro frame range data;
generating macro range angle images (RAIs) based on macro-Doppler frame range data; and
detecting a moving target based on the generated macro RAIs.

20. The method of claim 1, wherein L is equal to 32 and the second duration is about 3.2 seconds.

21. The method of claim 1, wherein the first target is a human target.

22. A method comprising:
receiving raw data from a millimeter-wave radar, the raw data comprising a plurality of macro-Doppler frames, each macro-Doppler frame having N chirps, N being a positive integer greater than 1, wherein each macro-Doppler frame stretches over a time interval having a first duration;
generating micro-Doppler frames from the plurality of macro-Doppler frames, each micro-Doppler frame comprising L chirps from M macro-Doppler frames, M being a positive integer greater than 1, L being a positive integer greater than 1, wherein each micro-Doppler frame stretches over a time interval having a second duration that is longer than the first duration;
detecting one or more moving targets based on the macro-Doppler frames;
detecting one or more static targets based on the micro-Doppler frames, wherein the second duration is selected to allow the micro-Doppler frames to include vital sign content of the one or more static targets;
determining whether a first target of the one or more moving targets detected based on the macro-Doppler frames stops moving; and
tracking the first target using the micro-Doppler frames only after the first target stops moving based on the determining.

23. A millimeter-wave radar comprising:
a transmitting antenna;
a plurality of receiving antennas;
a radar sensor configured to:
transmit radar signals using the transmitting antenna, and
receive reflected radar signals using the plurality of receiving antennas; and
a processor configured to:
receive raw data from the radar sensor, the raw data comprising a plurality of macro-Doppler frames, each macro-Doppler frame having N chirps, N being a positive integer greater than 1, wherein each macro-Doppler frame stretches over a time interval having a first duration,
generate micro-Doppler frames from the plurality of macro-Doppler frames, each micro-Doppler frame comprising L chirps from M macro-Doppler frames, M being a positive integer greater than 1, L being a positive integer greater than 1, wherein each micro-Doppler frame stretches over a time interval having a second duration that is longer than the first duration;
detect one or more moving targets based on the macro-Doppler frames;
detect one or more static targets based on the micro-Doppler frames;
determine whether a first target of the one or more moving targets detected based on the macro-Doppler frames stops moving; and
track the first target using the micro-Doppler frames only after the first target stops moving based on the determining, as the first target transitions from being detected based on the macro-Doppler frames to being detected based on the micro-Doppler frames.

24. A method for tracking a target, the method comprising:
receiving raw data from a millimeter-wave radar, the raw data comprising a plurality of macro-Doppler frames, each macro-Doppler frame having N chirps, N being a positive integer greater than 1, wherein each macro-Doppler frame stretches over a time interval having a first duration;
generating micro-Doppler frames from the plurality of macro-Doppler frames, each micro-Doppler frame comprising L chirps from M macro-Doppler frames, M being a positive integer greater than 1, L being a positive integer greater than 1, wherein each micro-Doppler frame stretches over a time interval having a second duration that is longer than the first duration;
detecting one or more moving targets based on the macro-Doppler frames;
detecting one or more static targets based on the micro-Doppler frames; and
tracking a first target as the target transitions from being detected based on the macro-Doppler frames to being detected based on the micro-Doppler frames, wherein the first target is in a first region, and tracking the first target comprises:
determining a first modal probability that a detected moving target in the first region is moving,
determining a second modal probability that a detected static target in the first region is static,
in response to the first modal probability being higher than the second modal probability, associating the first target to a moving state, the first target being tracked by a first track, and in response to the second modal probability being higher than the first modal probability, associating the first target to a static state.

25. A method for tracking a target, the method comprising:
receiving raw data from a millimeter-wave radar, the raw data comprising a plurality of macro-Doppler frames, each macro-Doppler frame having N chirps, N being a positive integer greater than 1, wherein each macro-Doppler frame stretches over a time interval having a first duration;
generating micro-Doppler frames from the plurality of macro-Doppler frames, each micro-Doppler frame comprising L chirps from M macro-Doppler frames, M being a positive integer greater than 1, L being a positive integer greater than 1, wherein each micro-Doppler frame stretches over a time interval having a second duration that is longer than the first duration;
detecting one or more moving targets based on the macro-Doppler frames;
detecting one or more static targets based on the micro-Doppler frames, detecting the one or more static targets comprising:
performing a range Fourier transform based on the micro-Doppler frames to generate micro-Doppler frame range data,
generating micro range angle images (RAIs) based on micro-Doppler frame range data, and
detecting the one or more static targets based on the generated micro RAIs, wherein generating the micro RAIs comprises generating a range-Doppler map, performing a two-dimensional (2D) moving target indication (MTI) filter on the range-Doppler map to generate a filtered range-Doppler map, and generating the micro RAIs based on the filtered range-Doppler map; and
tracking a first target as the target transitions from being detected based on the macro-Doppler frames to being detected based on the micro-Doppler frames.

26. A method for tracking a target, the method comprising:
receiving raw data from a millimeter-wave radar, the raw data comprising a plurality of macro-Doppler frames, each macro-Doppler frame having N chirps, N being a positive integer greater than 1, wherein each macro-Doppler frame stretches over a time interval having a first duration;
generating micro-Doppler frames from the plurality of macro-Doppler frames, each micro-Doppler frame comprising L chirps from M macro-Doppler frames, M being a positive integer greater than 1, L being a positive integer greater than 1, wherein each micro-Doppler frame stretches over a time interval having a second duration that is longer than the first duration;
detecting one or more moving targets based on the macro-Doppler frames;
detecting one or more static targets based on the micro-Doppler frames, detecting the one or more static targets comprising:
performing a range Fourier transform based on the micro-Doppler frames to generate micro-Doppler frame range data,
generating micro range angle images (RAIs) based on micro-Doppler frame range data, and
detecting the one or more static targets based on the generated micro RAIs, wherein generating the micro RAIs comprises generating a range spectrum, performing a one-dimensional (1D) moving target indication (MTI) filter on the range spectrum to generate a filtered range-Doppler map, and generating the micro RAIs based on the filtered range-Doppler map; and
tracking a first target as the target transitions from being detected based on the macro-Doppler frames to being detected based on the micro-Doppler frames.

* * * * *